(12) United States Patent
Sekar et al.

(10) Patent No.: US 12,188,081 B2
(45) Date of Patent: Jan. 7, 2025

(54) BIOINFORMATICS METHODS OF IN SILICO VALIDATION AND SELECTION OF CIRCRNAS

(71) Applicant: THE TRANSLATIONAL GENOMICS RESEARCH INSTITUTE, Phoenix, AZ (US)

(72) Inventors: Shobana Sekar, Phoenix, AZ (US); Winnie Liang, Phoenix, AZ (US); Jonathan Keats, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 800 days.

(21) Appl. No.: 16/752,115

(22) Filed: Jan. 24, 2020

(65) Prior Publication Data

US 2020/0239939 A1 Jul. 30, 2020

Related U.S. Application Data

(60) Provisional application No. 62/807,714, filed on Feb. 19, 2019, provisional application No. 62/796,491, filed on Jan. 24, 2019.

(51) Int. Cl.
| | | |
|---|---|---|
| *C12Q 1/6809* | (2018.01) | |
| *C12N 9/22* | (2006.01) | |
| *C12N 15/113* | (2010.01) | |
| *C12Q 1/686* | (2018.01) | |
| *G16B 30/00* | (2019.01) | |
| *G16B 50/30* | (2019.01) | |

(52) U.S. Cl.
CPC .............. *C12Q 1/6809* (2013.01); *C12N 9/22* (2013.01); *C12N 15/113* (2013.01); *C12Q 1/686* (2013.01); *G16B 30/00* (2019.02); *G16B 50/30* (2019.02); *C12N 2310/141* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 8,697,359 B1 | 4/2014 | Zhang |

FOREIGN PATENT DOCUMENTS

| | | |
|---|---|---|
| WO | 1988/009810 A1 | 12/1988 |
| WO | 1989/010134 A1 | 11/1989 |

OTHER PUBLICATIONS

Zheng et al (Genome Medicine, Published Jan. 19, 2019, 11:2, pp. 1-20).*
Panda, A.C. (2018). Chapter 6: Circular RNAs Act as miRNA Sponges. In: Xiao, J. (eds) Circular RNAs. Advances in Experimental Medicine and Biology, vol. 1087. Springer, Singapore. https://doi.org/10.1007/978-981-13-1426-1_6.*
Jeck, W. R., et al. Circular RNAs are abundant, conserved, and associated with ALU repeats. RNA 2013; 19(2):141-157.
Memczak, S., et al. Circular RNAs are a large class of animal RNAs with regulatory potency. Nature 2013; 495(7441):333-338.
Memczak, S., et al. Identification and Characterization of Circular RNAs As a New Class of Putative Biomarkers in Human Blood. PLoS One 2015; 10(10):e0141214.
Salzman, J., et al. Circular RNAs are the predominant transcript isoform from hundreds of human genes in diverse cell types. PLoS One 2012; 7(2):e30733.
Capel, B., et al. Circular transcripts of the testis-determining gene Sry in adult mouse testis. Cell 1993; 73(5):1019-1030.
Hansen, T.B., et al. Natural RNA circles function as efficient microRNA sponges. Nature 2013; 495(7441):384-388.
Hansen, T.B., et al. miRNA-dependent gene silencing involving Ago2-mediated cleavage of a circular antisense RNA. The EMBO Journal 2011; 30(21):4414-4422.
Du, W.W., et al. Foxo3 circular RNA promotes cardiac senescence by modulating multiple factors associated with stress and senescence responses. European Heart Journal 2016; 38(18):1402-1412.
Li, Z., et al. Exon-intron circular RNAs regulate transcription in the nucleus. Nature Structural & Molecular Biology 2015; 22(3):256-264.
Cheng, J., et al. Specific identification and quantification of circular RNAs from sequencing data. Bioinformatics 2016; 32(7):1094-1096.
Gao, Y., et al. CIRI: an efficient and unbiased algorithm for de novo circular RNA identification. Genome Biology 2015; 16:4.
Szabo, L., et al. Statistically based splicing detection reveals neural enrichment and tissue-specific induction of circular RNA during human fetal development. Genome Biology 2015; 16:126.
Wang, K., et al. MapSplice: accurate mapping of RNA-seq reads for splice junction discovery. Nucleic Acids Research 2010; 38(18):e178.
Zhang, X.O., et al. Complementary sequence-mediated exon circularization. Cell 2014; 159(1):134-147.
Chen, I., et al. Biogenesis, identification, and function of exonic circular RNAs. Wiley interdisciplinary reviews. RNA 2015;6(5):563-579.
Hansen, T.B., et al. Comparison of circular RNA prediction tools. Nucleic Acids Research 2016; 44(6):e58.
Zeng, X., et al. A comprehensive overview and evaluation of circular RNA detection tools. PLoS Computational Biology 2017; 13(6):e1005420.
Li, H., et al. The Sequence Alignment/Map format and SAMtools. Bioinformatics 2009; 25(16):2078-2079.
Haas, B. J., et al. De novo transcript sequence reconstruction from RNA-seq using the Trinity platform for reference generation and analysis. Nature Protocols 2013; 8(8):1494-1512.

(Continued)

*Primary Examiner* — Laura B Goddard
(74) *Attorney, Agent, or Firm* — Rodney J. Fuller; BOOTH UDALL FULLER, PLC

(57) ABSTRACT

The present invention relates to bioinformatics methods of in silico validation of circRNA junctions and selection of circRNA junctions for further validation, more particularly detecting sequence reads supporting circRNA junction in a highly computationally efficient manner.

18 Claims, 12 Drawing Sheets

(56) References Cited

OTHER PUBLICATIONS

Leinonen, R., et al. The Sequence Read Archive. Nucleic Acids Research 2011; 39(Database issue):D19-D21.

Langmead, B., et al. Fast gapped-read alignment with Bowtie 2. Nature Methods 2012; 9(4):357-359.

Beach, T. G., et al. Arizona study of aging and neurodegenerative disorders and brain and body donation program. Neuropathology 2015; 35(4):354-389.

Glazar, P., et al. circBase: a database for circular RNAs. RNA 2014; 20(11):1666-1670.

Li, H. Aligning sequence reads, clone sequences and assembly contigs with BWA-MEM. arXiv preprint arXiv:1303.3997 2013.

Salzman, J., et al. Cell-type specific features of circular RNA expression. PLoS Genetics 2013; 9(9):e1003777.

Szabo, L., et al. Detecting circular RNAs: bioinformatic and experimental challenges. Nature Reviews Genetics 2016; 17(11):679-692.

Westholm, J.O., et al. Genome-wide analysis of *Drosophila* circular RNAs reveals their structural and sequence properties and age-dependent neural accumulation. Cell Reports 2014; 9(5):1966-1980.

Wang, S., et al. Circular RNA FOXP1 promotes tumor progression and Warburg effect in gallbladder cancer by regulating PKLR expression. Molecular Cancer 2019; 18:145.

Liu, T., et al. Circular RNA has_circRNA_002178 silencing retards breast cancer progression via microRNA-328-3p-mediated inhibition of COL1A1. J Cell Mol Med 2020; 00:1-13.

Enright, A. J., et al. MicroRNA targets in *Drosophila*. Genome Biology 2003; 5:R I.

Rehmsmeier, M., et al. Fast and effective prediction of microRNA/target duplexes. RNA 2004; 10:1507-1517.

Karedath, T., et al. Silencing of ANKRD12 circRNA induces molecular and functional changes associated with invasive phenotypes. BMC Cancer 2019; 19:565.

Li, X., et al. The Biogenesis, Functions, and Challenges of Circular RNAs. Molecular Cell 2018; 71:428-442.

Ye, J. D., et al. Synthetic antibodies for specific recognition and crystallization of structured RNA. PNAS 2008; 105(1):82-87.

Sherman, E. M., et al. Specific RNA-Binding Antibodies with a Four-Amino-Acid Code. J Mol Biol 2014; 426:2145-2157.

Dominguez, D., et al. Sequence, Structure, and Context Preferences of Human RNA Binding Proteins. Molecular Cell 2018; 70:854-867.

Untergasser, A., et al. Primer3—new capabilities and interfaces. Nucleic Acids Research 2012; 40(15):e115.

Sand, M., et al. Circular RNA expression in cutaneous squamous cell carcinoma. J Dermatol Sci 2016; 83(3):210-218.

Lukiw, W. J. Circular RNA (circRNA) in Alzheimer's disease (AD). Front Genet 2013; 4:307.

Li, F., et al. Circular RNA ITCH has inhibitory effect on ESCC by suppressing the WNT/β-catenin pathway. Oncotarget 2015; 6(8):6001-6013.

Bachmayr-Heyda, A., et al. Correlation of circular RNA abundance with proliferation—exemplified with colorectal and ovarian cancer, idiopathic lung fibrosis, and normal human tissues. Sci Rep 2015; 5:8057.

Sekar, S., et al. Alzheimer's disease is associated with altered expression of genes involved in immune response and mitochondrial processes in astrocytes. Neurobiol Aging 2015; 36(2):583-591.

Sekar, S., et al. Circular RNA expression and regulatory network prediction in posterior cingulate astrocytes in elderly subjects. BMC Genomics 2018; 19:340.

Kristensen, L. S., et al. Circular RNAs in cancer: opportunities and challenges in the field. Oncogene 2018; 37(5):555-565.

Hammond, S. M., et al. Post-transcriptional gene silencing by double-stranded RNA. Nat Rev Genet 2001; 2(2):110-119.

Sharp, P. A. RNAi and double-strand RNA. Genes & Dev 1999; 13:139-141.

Bernstein, E., et al. Role for a bidentate ribonuclease in the initiation step of RNA interference. Nature 2001; 409(6818):363-366.

Elbashir, S. M., et al. RNA interference is mediated by 21- and 22-nucleotide RNAs. Genes Dev 2001; 15(2):188-200.

Tuschl, T. RNA interference and small interfering RNAs. Chembiochem 2001; 2(4):239-245.

Elbashir, S. M., et al. Duplexes of 21-nucleotide RNAs mediate RNA interference in cultured mammalian cells. Nature 2001; 411(6836):494-498.

Paddison, P. J., et al. Short hairpin RNAs (shRNAs) induce sequence-specific silencing in mammalian cells. Genes Dev 2002; 16(8):948-958.

Sui, G., et al. A DNA vector-based RNAi technology to suppress gene expression in mammalian cells. Proc Natl Acad Sci USA 2002; 99(8):5515-5520.

Brummelkamp, T. R., et al. A system for stable expression of short interfering RNAs in mammalian cells. Science 2002; 296(5567):550-553.

Paul, C. P., et al. Effective expression of small interfering RNA in human cells. Nature Biotechnol 2002; 20(5):505-508.

Summerton, J. Morpholino antisense oligomers: the case for an RNase H-independent structural type. Biochim Biophys acta 1999; 1489(1):141-158.

Summerton, J., et al. Morpholino antisense oligomers: design, preparation, and properties. Antisense Nucleic Acid Drug Dev 1997; 7(3):187-195.

Arora, V., et al. c-Myc antisense limits rat liver regeneration and indicates roles for c-Myc in regulating cytochrome P-450 3A activity. J Pharmacol Exp Ther 2000; 292:921-928.

Qin, G., et al. In Vivo Evaluation of a Morpholino Antisense Oligomer Directed Against Tumor Necrosis Factor-α. Antisense Nucleic Acid Drug Dev 2000; 10(1):11-16.

Heasman, J., et al. Beta-catenin signaling activity dissected in the early Xenopus embryo: a novel antisense approach. Dev Biol 2000; 222(1):124-134.

Nasevicius, A., et al. Effective targeted gene 'knockdown' in zebrafish. Nat Genet 2000; 26(2):216-220.

Nielsen, P. E., et al. Sequence-selective recognition of DNA by strand displacement with a thymine-substituted polyamide. Science 1991; 254(50347):1497-1500.

Jepsen, J. S., et al. LNA-antisense rivals siRNA for gene silencing. Curr Opin Drug Discov Devel 2004; 7(2):188-194.

Crinelli, R., et al. Locked Nucleic Acids (LNA): Versatile Tools for Designing Oligonucleotide Decoys with High Stability and Affinity. Curr Drug Targets 2004; 5(8):745-752.

Letsinger, R. L., et al. Cholesteryl-conjugated oligonucleotides: synthesis, properties, and activity as inhibitors of replication of human immunodeficiency virus in cell culture. Proc Natl Acad Sci USA 1989; 86(17):6553-6556.

Lemaitre, M., et al. Specific antiviral activity of a poly(L-lysine)-conjugated oligodeoxyribonucleotide sequence complementary to vesicular stomatitis virus N protein mRNA initiation site. Proc Natl Acad Sci USA 1987; 84(3):648-652.

Wiedenheft, B., et al. RNA-guided genetic silencing systems in bacteria and archaea. Nature 2012; 482(7385):331-338.

Amann, E., et al. Tightly regulated tac promoter vectors useful for the expression of unfused and fused proteins in *Escherichia coli*. Gene 1988; 69(2):301-315.

Baldari, C., et al. A novel leader peptide which allows efficient secretion of a fragment of human interleukin 1 beta in *Saccharomyces cerevisiae*. EMBO J 1987; 6(1):229-234.

Kurjan, J., et al. Structure of a yeast pheromone gene (MFα): A putative α-factor precursor contains four tandem copies of mature α-factor. Cell 1982; 30(3):933-943.

Schultz, L. D., et al. Expression and secretion in yeast of a 400-kda envelope glycoprotein derived from epstein-barr virus. Gene 1987; 54(1):113-123.

Seed, B. An LFA-3 cDNA encodes a phospholipid-linked membrane protein homologous to its receptor CD2. Nature 1987; 329(6142):840-842.

Kaufman, R. J., et al. Translational efficiency of polycistronic mRNAs and their utilization to express heterologous genes in mammalian cells. EMBO J 1987; 6(1):187-193.

Huston, J. S., et al. Antigen recognition and targeted delivery by the single-chain Fv. Cell Biophysics 1993; 22:189-224.

(56) References Cited

OTHER PUBLICATIONS

Pluckthun, A., et al. Expression of functional antibody Fv and Fab fragments in *Escherichia coli*. Meth Enzymol 1989; 178:497-515.
Koressaar, T., et al. Enhancements and modifications of primer design program Primer3. Bioinformatics 2007; 23(10): 1289-1291.

* cited by examiner

FIG. 2A Input a genome reference file

FIG. 2B Input a SAM File

FIG. 2C Align the assembled contig(s) to the pseudo reference

BIOINFORMATICS METHODS OF IN SILICO VALIDATION AND SELECTION OF CIRCRNAS

CROSS-REFERENCE TO RELATED APPLICATIONS

The present application claims priority to U.S. Provisional Patent Application No. 62/807,714, filed Feb. 19, 2019, and U.S. Provisional Patent Application No. 62/796,491, filed Jan. 24, 2019, the contents of each of which are hereby incorporated by reference in their entireties.

STATEMENT REGARDING FEDERALLY SPONSORED RESEARCH

This invention was made with governmental support under award number P30AG019610 awarded by the National Institute on Aging (NIA) of the National Institutes of Health (NIH). The United States government has certain rights in the invention.

TECHNICAL FIELD

The invention relates to bioinformatics methods of in silico validation of circRNA candidates. The invention also relates to bioinformatics methods of selecting circRNA candidates for further validation.

BACKGROUND OF THE INVENTION

Circular RNAs (circRNAs) are evolutionarily conserved RNA species that arise during post-transcriptional processes. A circRNA is formed when exons "back-splice" to each other, i.e., a single-stranded RNA molecule forms a circle through covalent binding. Recent rapid advances in high-throughput RNA sequencing (RNA-Seq) and global investigation of noncoding-linear (NCL) RNAs, has led to renewed interest in circRNAs, especially exonic circRNAs (ecircRNAs). There is growing evidence that circRNAs are not merely splicing intermediates, by-products, or products of aberrant splicing.

The emergence of high throughput RNA sequencing (RNA-Seq) technologies and bioinformatics algorithms has facilitated the identification of thousands of circRNAs in multiple cell and tissue types (Jeck et al., 2013; Memczak et al., 2013; Memczak et al., 2015; Salzman et al., 2012). These studies have found that circRNAs are highly abundant and evolutionarily conserved, as well as exhibit cell type- and developmental stage-specific expression. Some circRNAs, such as human CDR1as/ciRS-7 and circRNA of mouse Sry, were experimentally validated to function as microRNA (miRNA) sponges, and are thereby involved in gene expression regulation (Capel et al., 1993; Hansen et al., 2013; Hansen et al., 2011; Memczak et al., 2013). Furthermore, studies investigating their functional relevance have revealed that circRNAs can also act as decoys to RNA binding proteins (Du et al., 2016) and regulators of parental gene transcription (Li et al., 2015). Moreover, circRNAs are more stable than their linear counterparts since they are covalently closed loops without 5'/3' termini or a polyadenylated tail. For example, circRNAs were shown to be more stable than their linear counterparts in plasma and saliva, suggesting their potential as diagnostic biomarkers (Chen et al., 2015). Continued progress in improving the understanding of the biology of circRNAs will be crucial not only for functional analysis but also for the development of more accurate circRNA detection algorithms. Understanding the relationship between these circRNAs and their linear counterparts and their association with disease-forming processes will facilitate the development of diagnostic methods or therapies (Chen et al., 2015).

Current computational algorithms aimed at detecting circRNAs face several major challenges which hamper circRNA analysis. The use of different bioinformatics methods or sequencing data generated using different treatments produces divergent results. Hence, there is a need for novel methods that validate true circRNAs. As circRNAs continue to gain attention as an interesting class of novel non-coding RNA, development of novel methods, including in silico validation of candidate circRNA and selection of candidate circRNAs for experimental validation, are needed.

SUMMARY OF THE INVENTION

In certain aspects, the present invention relates to a bioinformatics method of validating a circRNA junction, comprising: receiving with a processor: a sequence file of a dataset comprising RNA sequencing (e.g., RNA-Seq) reads, a reference genome, and the circRNA junction; generating a plurality of contigs with the processor by: extracting start-reads and end-reads from the sequence file; and assembling the start-reads and end-reads into the plurality of contigs; generating a pseudo-reference with the processor by: extracting a start-sequence and an end-sequence from the reference genome; and concatenating the start-sequence and the end-sequence into the pseudo-reference; aligning the plurality of contigs to the pseudo-reference with the processor; and identifying an overlap between the plurality of contigs and the pseudo-reference to validate the circRNA junction.

In other aspects, the present invention provides a bioinformatics method of selecting a circRNA for further analysis comprising: receiving with a processor: a sequence file of a dataset comprising RNA sequencing (e.g., RNA-seq) reads, a reference genome, and a circRNA junction; extracting start-reads and end-reads from the sequence file with the processor; assembling a plurality of contigs from the start-reads and end-reads with the processor; extracting a start-sequence and an end-sequence from the reference genome with the processor; concatenating the start-sequence and the end-sequence into the pseudo-reference; aligning the plurality of contigs with the pseudo-reference; and selecting the circRNA for further analysis if the plurality of contigs overlap with the pseudo-reference.

In one aspect, the present invention further comprises performing RNA-Seq or whole transcriptome shotgun sequencing of RNA from a biological sample to obtain the RNA sequencing (e.g., RNA-Seq) reads. In certain aspects, the RNA is non-polyA selected. In other aspects, the RNA is treated with an exoribonuclease prior to performing RNA-Seq or whole transcriptome shotgun sequencing. In one aspect, the exoribonuclease is RNase R.

In some aspects, the biological sample is blood, plasma, serum, saliva, urine, sputum, ascites, semen, bronchial lavage fluid, synovial fluid, cerebrospinal fluid, cells, or tissue.

In other aspects, the circRNA is exonic. In yet other aspects, the circRNA is intergenic or intronic.

In some embodiments, the circRNA junction has been identified by a circRNA detection algorithm. In one embodiment, the circRNA junction is annotated.

In certain embodiments, the circRNA is at least 50 bp.

In some embodiments, the sequence file is selected from the group consisting of: a SAM (sequence alignment mapping) file, a BAM (binary alignment mapping) file, a CRAM file, Plain sequence format, FASTQ, EMBL format, FASTA format, GCG-rich sequence format (RSF), GenBank format, IG format, SFF, CSFASTA, SRF, and QSEQ. In one aspect, the sequence file is a SAM file.

In certain aspects, the sequence file comprises at least five million reads.

In some embodiments, extracting the start-reads and end-reads uses an extraction tool selected from the group consisting of SAMtools, BEDTools, Picard, Bio-SamTools, Pysam, BAMQL, Genomatix annotation syntax, Range Extractor DNA, getfasta, and homerTools. In one embodiment, the extraction tool is SAMtools.

In certain aspects, the length of the pseudo-reference is about 4 times the length of the insert size from a sequencing library produced with RNA-Seq or whole transcriptome shotgun sequencing in the sequence file. In other aspects, the length of the pseudo-reference is about 200 bp, about 300 bp, about 400 bp, about 500 bp, about 600 bp, about 700 bp, about 800 bp, about 900 bp, or about 1,000 bp.

In some embodiments, the present invention further comprises converting the end-reads and the start-reads into FASTQ with the processor.

In other embodiments, the plurality of contigs is generated using Trinity, Velvet/Oases, Bridger 25, Bridger 27, CLC, SoapDenovo, SOAPdenovo-Trans, Trans-AbySS, SPAdes, BinPacker, MIRA, STAble, IDP-denovo, CLC cell, or Newbler. In one aspect, the plurality of contigs is generated with Trinity.

In yet other aspects, at least two, at least three, at least four, at least five, at least six, at least seven, at least eight, at least nine, or at least ten end-reads and start-reads are extracted.

In some implementations, the database has a read length of at least 50 bp, at least 75 bp, at least 100 bp, at least 125 bp, at least 150 bp, or at least 175 bp. In other implementations, the data base has a read length of 50-300 bp or any number range in between, e.g., 50-250 bp, 50-200 bp 50-150 bp 100-300 bp, 100-250 bp, 100-200 bp, 100-150 bp, 150-300 bp, 150-250 bp, or 150-200 bp.

In some aspects, aligning the plurality of contigs to the pseudo-reference uses BWA-MEM, Bowtie, Bowtie2, STAR, TopHat, NovoAlign, Maq, GSNAP, GMAP, HISAT, or MapSplice. In one aspect, aligning the plurality of contigs to the pseudo-reference uses BWA-MEM.

In other aspects, the present invention further comprises determining if the overlap between the plurality of contigs and the pseudo-reference is above a threshold stringency. In some aspects, the threshold stringency requires a minimum of a 5-bp overlap, a 10-bp overlap, a 15-bp overlap, a 20-bp overlap, a 25-bp overlap, a 30-bp overlap, a 35-bp overlap, a 40-bp overlap, a 45-bp overlap, or a 50-bp overlap between the plurality of contigs and the pseudo-reference on either side of the circRNA junction.

In some embodiments, the processor comprises a Linux-based high-performance computing cluster. In one embodiment, the processor is capable of distributing data to an individual node within the cluster with an aggregate throughput of about 9 GB/sec.

In some aspects, the present invention further comprises experimentally validating the circRNA. In one embodiment, experimental validation uses polymerase chain reaction (PCR) to detect the presence of the circRNA, quantitative real-time PCR to quantify the abundance of the circRNA, or both. In another embodiment, experimental validation determines an in vivo loss-of-function circRNA phenotype by removing the circRNA locus.

In some aspects, the present invention further comprises functional studies of the circRNA. In one embodiment, a biomolecule that binds to the circRNA is identified. In another embodiment, a biomolecule that binds to the junction of the circRNA is identified.

To identify microRNAs (miRNA) that bind circRNAs, different bioinformatics tools are available such as miRanda (see Enright et al., "MicroRNA targets in Drosophila," Genome Biology 2003, 5:R1) and RNAHybrid (see Rehmsmeier et al., "Fast and effective prediction of microRNA/target duplexes," RNA (2004), 10:1507-1517). Predicted microRNA binding sites on circRNAs are identified based on complementarity in the miRNA seed region (nucleotide positions 2-7 at the miRNA 5' end). In certain embodiments, both miRanda and RNAHybrid are used and it is required that interactions be predicted by both tools. In other embodiments, it is required that interactions have an RNAHybrid predicted minimum free energy (MFE)<−20 and uncorrected P<0.05, along with a miRanda match score >=150 (see Sekar et al., "Circular RNA expression and regulatory network prediction in posterior cingulate astrocytes in elderly subjects," BMC Genomics (2018) 19:340).

In certain aspects, the biomolecule that binds to the circRNA is a microRNA (miRNA). In other aspects, a miRNA binding site on the circRNA is identified based on complementarity of a sequence of the circRNA with the miRNA seed region. In yet other aspects, the miRNA binding site on the circRNA is identified using miRanda and/or RNAHybrid.

In one embodiment, the function of the circRNA is determined from a loss-of-function phenotype. In another embodiment, the functional studies of the circRNA comprise overexpression and/or knockdown of the circRNA. Examples of experiments evaluating overexpression or knock-down of circRNA are presented in Wang et al., "Circular RNA FOXp1 promotes tumor progression and Warburg effect in gallbladder cancer by regulating PKLR expression," Molecular Cancer (2019) 18:145 and Liu et al., "Circular RNA hsa_circRNA_002178 silencing retards breast cancer progression via microRNA-328-3p-mediated inhibition of COL1A1," J Cell Mol Med. (2020) 00:1-13.

In certain aspects, the disclosed method further comprises generating a therapeutic agent targeting the circRNA. In some embodiments, the therapeutic agent comprises a small interfering RNA (siRNA), a CRISPR/CAS9 system, or an antibody or antigen-binding fragment.

In one aspect, the therapeutic agent is a siRNA targeting a circRNA junction. In another aspect, the therapeutic agent is a CRISPR/CAS9 system derived from *S. pyogenes* that targets the circRNA junction. In yet another aspect, the therapeutic agent is antibody or antigen-binding fragment recognizing a motif of up to 20 nucleotides with the motif comprising approximately 10 nucleotides or fewer on each side of a circRNA junction.

BRIEF DESCRIPTION OF THE DRAWINGS

(FIG. 2A) In phase 1A, a pseudo-reference containing the circRNA sequence of interest is generated from the reference genome. The pseudo-reference consists of $w_{ss}$ and $w_{es}$ bp from either side of the circRNA junction of interest (the dark and light grey blocks). The remaining portions of the exon that constitute the circRNA (the broken dark and light grey segments) are not part of the pseudo-reference. (FIG. 2B) In phase 1B, reads (end-reads from splice donor side and start-reads from splice acceptor side of the junction) within a user-defined window ($w_{er}$ bp for end-reads, $w_{sr}$ bp for start-reads) are extracted and assembled using Trinity. (FIG. 2C) In phase 2, the generated contigs are aligned to the pseudo-reference. The junction is validated or selected for further validation (e.g., experimental validation) if the overlap between the two sequences is above a user-defined threshold.

FIG. 5A and FIG. 5B presents the top and the bottom 200 candidates, respectively, based on the number of circRNA supporting reads.

DETAILED DESCRIPTION

Figure 1:
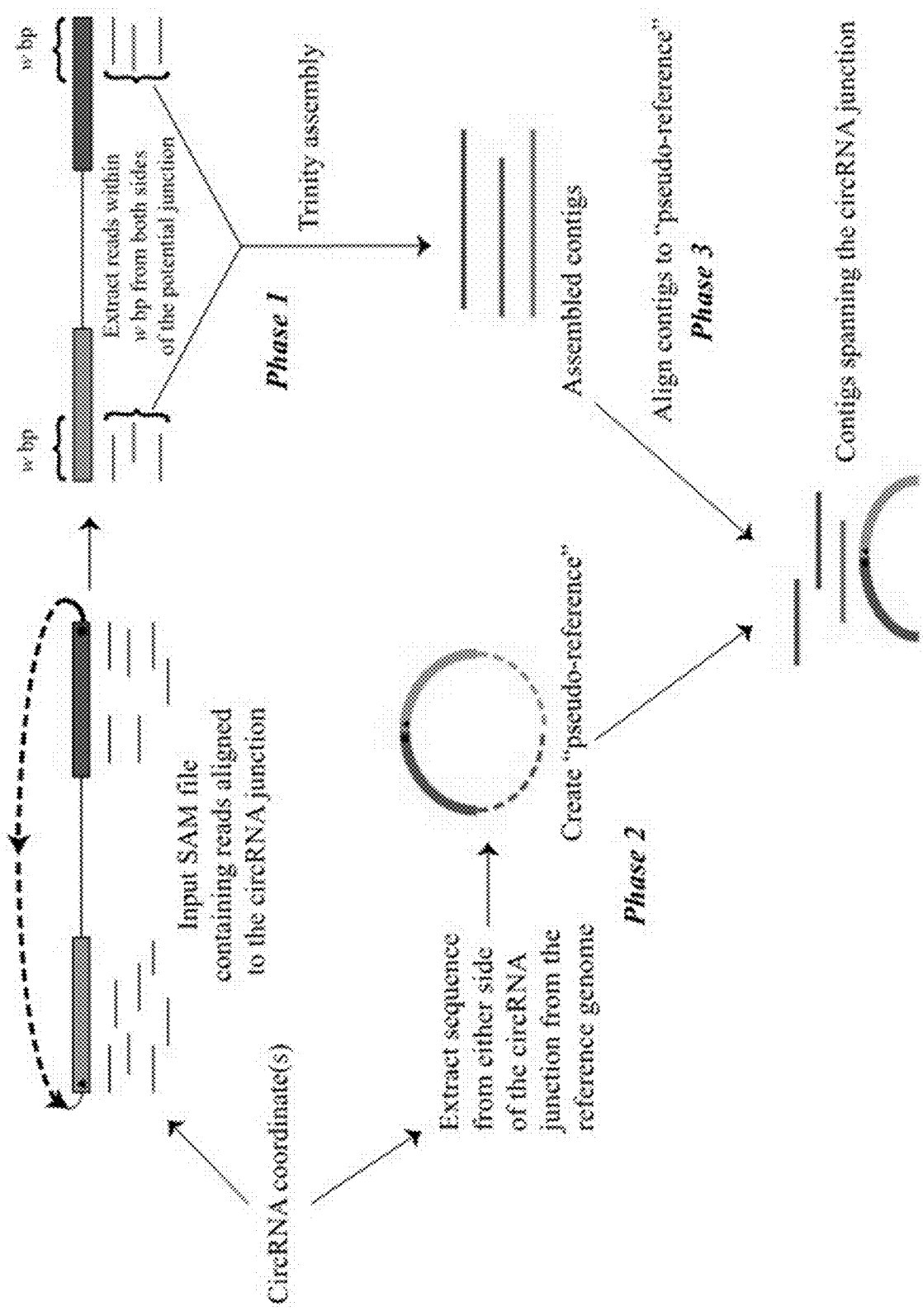
FIG. 1 depicts a non-limiting embodiment of the ACValidator workflow. ACValidator takes as input the sequence alignment mapping (SAM) file and the circRNA junction coordinate(s) to be validated. In phase 1, reads from either side of the junction within a user-defined window (w) are extracted and generated using Trinity. A pseudo-reference containing the circRNA sequence of interest is generated from the reference genome in phase 2. The pseudo-reference consists of w bp from either side of the circRNA junction of interest (solid blue and pink blocks). The broken blue and pink segments represent the remaining portions of the exon that constitute the circRNA (these segments are not part of the pseudo-reference). Lastly, in phase 3, the generated contigs are aligned to this pseudo-reference and checked for overlap with the sequence of the junction to be validated.

The verb "comprise" as is used in this description and the claims and its conjugations are used in its non-limiting sense to mean that items following the word are included, but items not specifically mentioned are not excluded. Also, reference to an element by the indefinite article "a" or "an" does not exclude the possibility that more than one of the elements is present unless the context clearly requires that there is one and only one of the elements. The indefinite article "a" or "an" thus usually means "at least one."

The term "contigs" as used herein, refers to contiguous regions of DNA sequence. "Contigs" can be determined by any number methods known in the art, such as, by comparing sequencing reads for overlapping sequences, and/or by comparing sequencing reads against databases of known sequences in order to identify which sequencing reads have a high probability of being contiguous. Contigs are often generated by assembling individual sequence reads or previously assembled sequence information in combination with sequence reads having overlapping end or edge sequence. Generally but not exclusively, contigs comprise overlapping sequence reads that assemble into a larger sequence grouping, in many cases without intervening gaps or regions of undetermined sequence, or alternately without regions of known sequence and unknown length.

As used herein, "circular RNAs" or "circRNAs" refer to a type of RNA that forms a covalently closed continuous loop via joining of the 3' and 5' ends of two exons/introns or exon/intron fragments. CircRNAs include exonic circRNAs (ecircRNAs) and intronic circRNAs. A circRNA has a "start-coordinate" at its 5' end and an "end-coordinate" at its 3' end prior to ligation or splicing of these two ends. CircRNAs typically arise from otherwise protein-coding genes (i.e., exons), but circRNAs have not been shown to be translated in vivo. Accordingly, circRNAs are considered to be noncoding RNA. Because circular RNAs do not have 5' or 3' ends, they are generally resistant to exonuclease-mediated degradation.

As used herein, the term "circRNA junction" refers to a region formed between the 5'-head of a first exon or a first intron (i.e., the "start-coordinate") and the 3'-tail of a second exon or a second intron (i.e., the "end-coordinate") in a circRNA. A circRNA junction represents a unique sequence generated by ligation or splicing, which should not be present in the genome or mRNAs of an organism.

The term "read" or "sequencing read" as used herein, refers to sequence information of a segment of DNA or RNA for which the sequence has been determined.

As used herein, the term "start-read" refers to a read beginning at or near (e.g., within 5, 10, 15, 20, 25, 30, 35, 40, 45, or 50 bp of) a "start-coordinate" of a circRNA and ending a number (w or $w_{sr}$) of bp downstream of the "start-coordinate."

In some embodiments, the start-read begins at the start-coordinate. In other embodiments, the start-read begins near the start-coordinate, e.g., within 1-20 bp of the start-coordinate, or any number range in between, e.g., 2-20 bp, 2-15 bp, 3-15 bp, 3-10 bp, 4-10 bp, 4-8 bp, or 5-8 bp, etc. In yet other embodiments, the start-read begins within less than 50 bp, less than 40 bp, less than 30 bp, less than 20 bp, less than 10 bp, or less than 5 bp of the start-coordinate, etc.

The value of w or $w_{sr}$ is user-defined. In some implementations, w or $w_{sr}$ is about 2 times the length of an insert size of the sequence file, for example, 1-5 times, 1-4 times, 1.5-4 times, 1.5-3 times, or 2-3 times, etc. In other implementations, w or $w_{sr}$ is about 100 bp, about 150 bp, about 200 bp, about 250 bp, about 300 bp, about 350 bp, or about 400 bp. In yet other implementations, w or $w_{sr}$ is 100-600 bp, or any number range in between, e.g., 100-500 bp, 150-500 bp, 150-450 bp, 200-450 bp, 200-400 bp, or 300-400 bp, etc.

As used herein, the term "end-read" refers to a read ending at or near (e.g., within 5, 10, 15, 20, 25, 30, 35, 40, 45, or 50 bp of) an "end-coordinate" of a circRNA and starting a number (w or $w_{er}$) of bp upstream of the "end-coordinate."

In some embodiments, the end-read ends at the end-coordinate. In other embodiments, the end-read ends near the end-coordinate, e.g., within 1-20 bp of the end-coordinate, or any number range in between, e.g., 2-20 bp, 2-15 bp, 3-15 bp, 3-10 bp, 4-10 bp, 4-8 bp, or 5-8 bp, etc. In yet other embodiments, the end-read ends within less than 50 bp, less than 40 bp, less than 30 bp, less than 20 bp, less than 10 bp, or less than 5 bp of the end-coordinate, etc.

The value of w or $w_{er}$ is user-defined. In some implementations, w or $w_{er}$ is about 2 times the length of an insert size of the sequence file, for example, 1-5 times, 1-4 times, 1.5-4 times, 1.5-3 times, or 2-3 times, etc. In other implementations, w or $w_{er}$ is about 100 bp, about 150 bp, about 200 bp, about 250 bp, about 300 bp, about 350 bp, or about 400 bp. In yet other implementations, w or $w_{er}$ is 100-600 bp, or any number range in between, e.g., 100-500 bp, 150-500 bp, 150-450 bp, 200-450 bp, 200-400 bp, or 300-400 bp, etc. In one embodiment, $w_{sr}=w_{er}$.

The term "start-sequence" as used herein refers to a sequence from a reference genome beginning at a "start-coordinate" of a circRNA and ending a number (w or $w_{ss}$) of bp downstream of the "start-coordinate." In some embodiments, the start-sequence begins at the start-coordinate. In other embodiments, the start-sequence begins near the start-coordinate, e.g., within 1-20 bp of the start-coordinate, or any number range in between, e.g., 2-20 bp, 2-15 bp, 3-15 bp, 3-10 bp, 4-10 bp, 4-8 bp, 5-8 bp, etc. In yet other embodiments, the start-sequence begins within less than 50 bp, less than 40 bp, less than 30 bp, less than 20 bp, less than 10 bp, or less than 5 bp of the start-coordinate, etc.

The value of w or $w_{ss}$ is user-defined. In some implementations, w or $w_{ss}$ is about 2 times the length of an insert size of the sequence file, for example, 1-5 times, 1-4 times, 1.5-4 times, 1.5-3 times, or 2-3 times, etc. In other implementations, $w_{ss}$ is about 100 bp, about 150 bp, about 200 bp, about 250 bp, about 300 bp, about 350 bp, or about 400 bp. In yet other implementations, w or $w_{ss}$ is 100-600 bp, or any number range in between, e.g., 100-500 bp, 150-500 bp, 150-450 bp, 200-450 bp, 200-400 bp, or 300-400 bp, etc.

The term "end-sequence" as used herein refers to a sequence from a reference genome ending at an "end-coordinate" of a circRNA and starting a number (w or $w_{es}$) of bp upstream of the "end-coordinate."

The value of w or $w_{es}$ is user-defined. In some implementations, w or $w_{es}$ is about 2 times the length of an insert size of the sequence file, for example, 1-5 times, 1-4 times, 1.5-4 times, 1.5-3 times, or 2-3 times, etc. In other implementations, w or $w_{es}$ is about 100 bp, about 150 bp, about 200 bp, about 250 bp, about 300 bp, about 350 bp, or about 400 bp. In yet other implementations, w or $w_{es}$ is 100-600 bp, or any number range in between, e.g., 100-500 bp, 150-500 bp, 150-450 bp, 200-450 bp, 200-400 bp, or 300-400 bp, etc. In one embodiment, $w_{ss}=w_{es}$. In one implementation, $w_{ss}=w_{es}=w_{sr}=w_{er}$.

Several computational tools have been developed to identify the "back-splicing" events in RNA-Seq data. Strategies employed by these computational tools to identify circRNAs include: 1) a pseudo-reference-based strategy, which is used by KNIFE (Szabo et al., 2015); and 2) a fragment-based strategy, which is used by find_circ (Memczak et al., 2013), CIRCexplorer (Zhang et al., 2014), Mapsplice (Wang et al., 2010), and DCC (Cheng et al., 2016). While KNIFE constructs a pseudo-reference of all possible out-of-order exons to align reads against, fragment-based strategies detect circRNAs based on the mapping information of a split read's alignment to the reference genome (Chen et al., 2015). When segments of a split read align to the reference in a non-colinear order, they are marked as potential circRNA candidates. Apart from these strategies, CIRI uses CIGAR (concise idiosyncratic gapped alignment report) signatures in the alignment file to identify circRNAs (Gao et al., 2015).

For the pseudo-reference-based strategy, genome annotation is required. All possible combinations of pseudo references are constructed; each of them is comprised of two well-annotated exons in which the exon order is topologically inconsistent with the reference genome (Chen et al., 2015). A pseudo-reference is regarded as a circRNA candidate if it has at least one read that maps to its non-colinear junction site (Chen et al., 2015). The pseudo-reference-based methods have two major limitations. First, circRNAs with unannotated exon junctions cannot be identified. Second, they are not suitable for detection of circRNAs in genomes that are incompletely or poorly annotated.

The fragment-based strategy detects circRNAs without the help of genome annotation. RNA-Seq reads (each paired-end read is viewed as two 'single' reads) are split into two or more segments, and each segment is mapped to the reference genome; segmented reads mapped in an NCL manner are retained (Chen et al., 2015). The fragment-based methods also have two major limitations. First, they are more likely to yield alignment errors (or ambiguity) than the pseudo-reference-based methods while performing read-to-genome alignment, because segmented reads are smaller than full-length reads. Second, NCL junctions that do not match annotated exon boundaries tend to be unreliable and are more likely to originate from mis-splicing.

Tool comparison studies have revealed that existing circRNA detection algorithms produce divergent results due to the use of different aligners, heuristics and filtering criteria (Hansen et al., 2016; Zeng et al., 2017). Hence, there is a need for in silico validation methods that can distinguish true versus false positive circRNAs identified using these algorithms.

In one aspect of the present disclosure, there is provided a method of validating a circRNA junction using a processor. Typically, the method comprises, receiving a sequence file comprising RNA sequence reads, a reference genome, and the circRNA junction; generating a plurality of contigs; generating a pseudo-reference; aligning the plurality of contigs to the pseudo-reference; and identifying an overlap between the plurality of contigs and the pseudo-reference, wherein generating the plurality of contigs comprises extracting start-reads and end-reads from the sequence file, and assembling the start-reads and end-reads into the plurality of contigs; and generating the pseudo-reference comprises extracting a start-sequence and an end-sequence from the reference genome, and concatenating the start-sequence and the end-sequence into the pseudo-reference.

In another aspect of the present disclosure, there is provided a method of selecting a circRNA junction for further analysis. Typically, the method comprises receiving a sequence file comprising RNA sequence reads, a reference genome, and the circRNA junction with a processor; extracting start-reads and end-reads from the sequence file with the processor; assembling a plurality of contigs from the start-reads and end-reads with the processor; extracting a start-sequence and an end-sequence from the reference genome with the processor; concatenating the start-sequence and the end-sequence into the pseudo-reference with the processor; aligning the plurality of contigs with the pseudo-reference with the processor; and selecting the circRNA junction for further analysis if the plurality of contigs overlap with the pseudo-reference.

Possible models of circRNA biogenesis include lariat-driven circularization, intron-pairing-driven circularization, and resplicing-driven circularization (Chen et al., 2015). CircRNAs typically arise from otherwise protein-coding genes (i.e., exons), but circRNAs have not been shown to be translated in vivo. Accordingly, circRNAs are considered to be noncoding RNA. Because circular RNAs do not have 5' or 3' ends, they are generally resistant to exonuclease-mediated degradation. In some aspects, the circRNA is exonic. In other aspects, the circRNA is intergenic or intronic. In further aspects, the circRNA comprises at least 40 base pairs, at least 45 base pairs, at least 50 base pairs, at least 75 base pairs, least 100 base pairs, or least 200 base pairs.

In some embodiments, the method further comprises identifying the circRNA junction using a circRNA detection algorithm. Non-limiting examples of circRNA detection algorithms include CIRCexplorer, CIRI, DCC, find_circ, KNIFE, MapSplice, Segemehl, or Tophat-Fusion, etc. In further embodiments, the circRNA junction is annotated.

In some implementations, the RNA sequencing reads are obtained from one dataset. In other implementations, the RNA sequencing reads are obtained from two, three, four, five, or six or more datasets. In some implementations, the RNA is non-polyA selected. As used herein, "non-polyA selected" refers to enriching for non-polyadenylated RNA populations. In other implementations, the RNA is treated with an exoribonuclease, e.g., RNase R. In further implementations, the RNA is both non-polyA selected and treated with RNase R.

In some embodiments, the method further comprises generating RNA sequence reads, for example, by performing RNA-Seq or whole transcriptome shotgun sequencing from a biological sample. As used herein, the term "generating sequence reads" refers to determining the identity and order of at least two nucleotide bases. Non-limiting examples of biological samples include cell, tissue, blood, plasma, serum, saliva, urine, sputum, ascites, semen, bronchial lavage fluid, synovial fluid, cerebrospinal fluid, or combinations thereof, etc.

In some implementations, the sequence file comprises at least two million reads, at least five million reads, at least 10 million reads, at least 15 million reads, at least 20 million reads, or at least 25 million reads. In other implementations, the sequence file comprises 2-25 million reads, or any number in between, e.g., 2-20 million reads, 3-20 million reads, 3-15 million reads, 4-15 million reads, 4-10 million reads, 5-10 million reads, or 5-8 million reads, etc.

In some embodiments, the sequence file has a file format selected from the group consisting of SAM (sequence alignment mapping) file, BAM (binary alignment mapping) file, CRAM file, Plain sequence format, FASTQ, EMBL format, FASTA format, GCG-rich sequence format (RSF), GenBank format, IG format, SFF, CSFASTA, SRF, and QSEQ. In preferred embodiments, the file format is SAM file. In some implementations, the method further comprises evaluating the sequence file, filtering the sequence file, pre-processing the sequence file (e.g., using cutAdapt), or combinations thereof.

In some embodiments, extracting the start-reads and end-reads uses an extraction tool. Non-limiting examples of extraction tools include SAMtools, BEDTools, Picard, Bio-SamTools, Pysam, BAMQL, Genomatix annotation syntax, Range Extractor DNA, getfasta, or homerTools, etc. In preferred embodiments, the extraction tool is SAMtools.

In some implementations, the method further comprises converting the end-reads and the start-reads into FASTQ with the processor.

In other implementations, at least three, at least four, at least five, at least six, at least seven, at least eight, at least nine, or at least ten end-reads and start-reads are extracted. In preferred implementations, at least five end-reads and start-reads are extracted.

In some embodiments, the plurality of contigs is generated using an assembly tool. Non-limiting examples of assembly tool include Trinity, Velvet/Oases, Bridger 25, Bridger 27, CLC, SoapDenovo, SOAPdenovo-Trans, Trans-AbySS, SPAdes, BinPacker, MIRA, STAble, IDP-denovo, CLC cell, or Newbler, etc. In preferred embodiments, the assembly tool is Trinity.

As used herein, the term "reference genome" refers to a digital nucleic acid sequence database, assembled as a representative example of a species' set of genes. CircRNAs have also been reported in plants, primates, pigs, etc., and any organism that has DNA could potentially have circRNAs. In some aspects, the circular RNA is a human RNA. Non-limiting examples of human reference genomes include GRCh38, GRCh37, NCBI Build 36.1, NCBI Build 35, or NCBI Build 34, etc. In other aspects, the circular RNA is a mouse RNA. Non-limiting examples of mouse reference genomes include GRCm38, NCBI Build 37, NCBI Build 36, NCBI Build 35, or NCBI Build 34, etc.

In some embodiments, the length of the pseudo-reference is about 4 times the length of the insert size of the sequence file, for example, 1-10 times, 1-8 times, 2-8 times, 2-6 times, 3-5 times, or 3-4 times, etc. In other embodiments, the length of the pseudo-reference is about 200 bp, about 300 bp, about 400 bp, about 500 bp, about 600 bp, about 700 bp, about 800 bp, about 900 bp, or about 1,000 bp. In yet other embodiments, the length of the pseudo-reference is 100-1,200 bp, or any number range in between, e.g., 100-10,00 bp, 200-1,000 bp, 200-900 bp, 300-900 bp, 300-800 bp, 400-800 bp, 400-700 bp, or 500-700 bp, etc.

In some implementations, aligning the plurality of contigs to the pseudo-reference uses an alignment tool. Non-limiting examples of alignment tools include BWA-MEM, Bowtie, Bowtie2, STAR, TopHat, NovoAlign, Maq, GSNAP, GMAP, HISAT, or MapSplice, etc. In preferred implementations, the alignment tool is BWA-MEM.

In some embodiments, the method further comprises determining if the overlap between the plurality of contigs and the pseudo-reference is above a threshold stringency. In some implementations, the threshold stringency requires a minimum of a 5-bp overlap, a 10-bp overlap, a 15-bp overlap, a 20-bp overlap, a 25-bp overlap, a 30-bp overlap, a 35-bp overlap, a 40-bp overlap, a 45-bp overlap, or a 50-bp overlap between at least two, at least three, at least four, at least five, at least six, at least eight, or at least ten of the plurality of contigs and the pseudo-reference on either side of the circRNA junction.

In an alternative aspect of the present disclosure, there is provided a method of validating a circRNA junction or selecting a circRNA junction for further analysis. Typically, the method comprises, receiving a sequence file comprising RNA sequence reads, a reference genome, and the circRNA junction with a processor; extracting start-reads and end-reads from the sequence file with the processor; extracting a start-sequence and an end-sequence from the reference genome with the processor; aligning the start-reads to the start-sequence; identifying an overlap between the start-reads and the start-sequence; aligning the end-reads to the end-sequence; and identifying an overlap between the end-reads and the end-sequence.

In some embodiments, the method further comprises determining if the overlap between the start-reads and the start-sequence and the end-reads and the end-sequence are above a threshold stringency. In some implementations, the threshold stringency requires a minimum of a 5-bp overlap, a 10-bp overlap, a 15-bp overlap, a 20-bp overlap, a 25-bp overlap, a 30-bp overlap, a 35-bp overlap, a 40-bp overlap, a 45-bp overlap, or a 50-bp overlap between at least two, at least three, at least four, at least five, at least six, at least eight, or at least ten of the start reads and the start-sequence and between at least two, at least three, at least four, at least five, at least six, at least eight, or at least ten of the end-reads and the end-sequence.

In some implementations, the database has a read length of at least 50 bp, at least 75 bp, at least 100 bp, at least 125 bp, at least 150 bp, or at least 175 bp. In other implementations, the data base has a read length of 50-300 bp or any number range in between, e.g., 50-250 bp, 50-200 bp 50-150 bp 100-300 bp, 100-250 bp, 100-200 bp, 100-150 bp, 150-300 bp, 150-250 bp, or 150-200 bp.

As used herein, "a processor" refers to one or more logic circuitries that respond to and process the basic instructions that drive a computer. In some embodiments, the processor comprises a Linux-based high-performance computing cluster. In further embodiments, the processor is capable of distributing data to an individual node within the cluster with an aggregate throughput of about 6 GB/sec, about 7 GB/sec, about 8 GB/sec, about 9 GB/sec, about 10 GB/sec, or about 12 GB/sec, etc.

In certain aspects, the method further comprises experimentally validating the circRNA junction. A non-limiting example of an experimental validation is the use of PCR (e.g., qRT-PCR) to detect the presence and/or quantify the abundance of the circRNA of interest.

In certain aspects, after validating the sequence of the circRNA junction functional studies are performed. A non-limiting example is determining the in vivo functional consequence of loss-of-function circRNA phenotype (e.g., by removing the circular RNA locus from the genome). Another non-limiting example of a functional study is the use of the sequence of the circRNA junction as a probe to identify a biomolecule (e.g., DNA, RNA, such as a micro RNA or a long non-coding RNA, or a protein) that binds to the circRNA. In one aspect, the probe is bound to a matrix and used to extract the biomolecule from a complex mixture (e.g., a cell extract, a tissue extract, etc.). In another aspect, the probe is labeled (e.g., with a fluorescent tag, enzyme, epitope, etc.) and is added to a biological sample, cell population, or cell extract to bind to and identify circRNA binding partners. In another aspect, photoreactive ribonucleoside analogs, such as 4-thiouridine (4-SU) and 6-thioguanosine (6-SG), are incorporated into nascent RNA transcripts by living cells. For example, after validating the sequence of the circRNA junction, Photoactivatable Ribonucleoside-Enhanced Crosslinking and Immunoprecipitation (PAR-CLIP) is used to confirm circRNA-protein interactions. In another aspect, miRNA seed matching analyses are used to identify miRNA-circRNA binding.

In some embodiments, the functional study comprises querying of circRNA sequences against known gene sequences to identify genes or transcripts that are regulated by specific circRNAs. Identification of regulated genes allows for the identification of biological processes and pathways that circRNAs influence.

In other embodiments, after a circRNA is identified as binding to proteins and/or affecting translation, this capability is exploited such as through depletion of circRNAs to potentially increase translation of specific proteins and/or introduction of more circRNAs (e.g., activation of upstream transcriptional processes or through the use of vectors) to inhibit translation of specific proteins.

In other embodiments, the identified circRNAs are used as biomarkers for tissue types or disease conditions. For example, circRNAs are known to be highly expressed in the brain such that if there is neurodegeneration and the blood-brain-barrier is compromised, degenerating cells may release circRNAs into the blood or cerebrospinal fluid (CSF) and act as a marker for disease. In the area of cancer, circRNAs may serve as prognostic and diagnostic biomarkers given their widespread expression as well as therapeutic targets (see Kristensen et al., "Circular RNAs in cancer: opportunities and challenges in the field," (2018) Oncogene 37(5):555-565).

In certain aspects, the disclosed methods further comprise generating a therapeutic agent targeting the circRNA. In one aspect, the therapeutic agent comprises a small interfering RNA (siRNA). In another aspect, multiple siRNAs against the circRNA are designed to increase the likelihood of knockdown. In yet another aspect, the therapeutic agent comprises a CRISPR/Cas9 system.

In some embodiments, the therapeutic agent inhibits the action of a circRNA through binding of the circRNA molecule and/or depletion of the circRNA molecule. In other embodiments, the therapeutic agent is an engineered circRNA that is introduced into a biological system. In certain aspects, the therapeutic agent corrects the sequence of a circRNA, such as with a CRISPR-CAS9 system. In other aspects, the therapeutic agent is a genetic vector providing for the introduction or increased expression of a circRNA.

RNA interference (RNAi) is a process of sequence-specific post-transcriptional gene silencing by which double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing is mediated by short double-stranded small interfering RNAs (siR-NAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). For mammalian systems, RNAi commonly involves the use of dsRNAs that are greater than 500 bp; however, it can also be activated by introduction of either siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The siRNAs of the present invention are preferably short double stranded nucleic acid duplexes comprising annealed complementary single stranded nucleic acid molecules. In preferred embodiments, the siRNAs are short dsRNAs comprising annealed complementary single strand RNAs. However, the invention also encompasses embodiments in which the siRNAs comprise an annealed RNA:DNA duplex, wherein the sense strand of the duplex is a DNA molecule and the antisense strand of the duplex is a RNA molecule.

In some embodiments, duplexed siRNAs have a 2 or 3 nucleotide 3' overhang on each strand of the duplex. In some embodiments, siRNAs have 5'-phosphate and 3'-hydroxyl groups.

The siRNA molecules of the invention may include one or more modifications (e.g., to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and LNA. Where the siRNA molecule is produced synthetically, or by in vitro transcription, a modified ribonucleoside may be introduced during synthesis or transcription.

Non-limiting examples of modified base moieties include inosine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Non-limiting examples of modified sugar moieties include arabinose, 2-fluoroarabinose, xylulose, and hexose. Modified siRNAs may contain substituted sugar moieties comprising one of the following at the 2' position: OH, SH, SCH$_3$, F, OCN, O(CH$_2$)$_n$NH$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O—; S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified siRNAs may also have sugar mimetics such as cyclobutyls or other carbocyclics in place of the pentofuranosyl group.

Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with CH$_2$—NH—O—CH$_2$, CH$_2$—N(CH$_3$)—O—CH$_2$, CH$_2$—O—N (CH$_3$)—CH$_2$, CH$_2$—N(CH$_3$)—N(CH$_3$)—CH$_2$ and O—N (CH$_3$)—CH$_2$—CH$_2$ backbones (where phosphodiester is —O—PO$_2$—O—CH$_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

Also envisioned are modified siRNA molecules having morpholino backbone structures in which the bases are linked to 6-membered morpholine rings, which are connected to other morpholine-linked bases via non-ionic phosphorodiamidate intersubunit linkages. Morpholino siRNAs are highly resistant to nucleases and have good targeting predictability (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability.

Modified siRNAs can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810) or blood-brain barrier (see, e.g., PCT Publication No. WO 89/10134), etc.

According to the present invention, siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

In some aspects, the method further comprises designing an siRNA targeting the circRNA junction sequence. Designing an siRNA uses the same process as is used for targeting mRNAs except the target sequence would simply be the circRNA junction sequence (see, for example, FIG. 1a in Karedath et al., "Silencing of ANKRD12 circRNA induces molecular and functional changes associated with invasive phenotypes," BMC Cancer (2019) 19:565).

Design of an siRNA requires starting with a 21 nucleotide long sequence to target—this sequence would flank the circRNA junction of a circRNA. In some embodiments, this involves testing various lengths of flanking sequence on each side the circRNA junction to determine which lengths provide optimal silencing. In some aspects, at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, or at least 10 nucleotides on each side of the junction are required. SiRNA design is also influenced by the sequence itself; e.g. stretches of four U's or A's should be avoided in the target sequence.

In some embodiments, the therapeutic agent targeting the circRNA is a Clustered Regularly Interspaced Short Palindromic Repeats (CRISPR)/CAS9 system described, for example, in Wiedenheft et al., "RNA-guided genetic silencing systems in bacteria and archaea," Nature 482 (7385): 331-8 (2012) and in Li et al., "The Biogenesis, Functions, and Challenges of Circular RNAs," Mol Cell. 71(3):428-442 (2018), the entireties of which are incorporated herein by reference. In other aspects, functional study of the circRNA comprises knock-down or knock-out of the circRNA with a CRISPR/CAS9 system.

Briefly, an engineered, programmable, non-naturally occurring CRISPR-Cas system comprising a Cas9 protein and one or more guide RNAs that target the circRNA in a eukaryotic cell is provided, and the Cas9 protein binds to and/or cleaves the circRNA, altering expression and/or activity of the circRNA (see U.S. Pat. No. 8,697,359, the entirety of which is incorporated herein by reference).

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism.

In some embodiments, the vectors are fusion expression vectors. Examples of such vectors include, but are not limited to, commercially available vectors such as pGEX (Pharmacia Biotech Inc), pMAL (New England Biolabs) and pRITS (Pharmacia, Piscataway, N.J.) that fuse glutathione S-transferase (GST), maltose E binding protein, or protein A. respectively, to the target recombinant protein. Examples of suitable inducible non-fusion *E. coli* expression vectors include, but are not limited to, pTrc (Amrann et al., Gene 69:301-315 (1988)) and pET 11d (Studier et al., GENE EXPRESSION TECHNOLOGY: METHODS IN ENZYMOLOGY 185, Academic Press, San Diego, Calif. 60-89 (1990)).

In some embodiments, a vector is a yeast expression vector. Examples of such vectors include, but are not limited to, pYepSec1 (Baldari et al., EMBO J. 6: 229-234 (1987)), pMfa (Kuijan and Herskowitz, 1982. Cell 30: 933-943), pJRY88 (Schultz et al., Gene 54: 113-123 (1987)), pYES2 (Invitrogen Corporation, San Diego, Calif.), and picZ (Invitrogen Corp, San Diego, Calif.).

In some embodiments, vectors are mammalian expression vectors. Examples such vectors include, but are not limited to, pCDM8 (Seed, Nature 329: 840 (1987)) and pMT2PC (Kaufman et al., EMBO J. 6: 187-195 (1987)). When used in mammalian cells, the expression vector's control functions are typically provided by one or more regulatory elements. For example, commonly used promoters are derived from polyoma, adenovirus 2, cytomegalovirus, simian virus 40, and others known in the art.

In some embodiments, a regulatory element is operably linked to one or more elements of a CRISPR system so as to drive expression of the one or more elements of the CRISPR system. CRISPR loci have been identified in more than 40 prokaryotes including, but not limited to, *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*.

Typically, a CRISPR system is characterized by elements that promote the formation of a CRISPR complex at the site of a target sequence (also referred to as a protospacer in the context of an endogenous CRISPR system). The term "target sequence," when used in connection with CRISPR system, refers to a sequence to which a guide sequence is designed to have complementarity, where hybridization between a target sequence and a guide sequence promotes the formation of a CRISPR complex. In some embodiments, full complementarity may not be necessary, provided there is sufficient complementarity to cause hybridization and promote formation of a CRISPR complex. In other embodiments, the target sequence comprises the circRNA junction.

A target sequence may comprise any polynucleotide, such as DNA or RNA polynucleotides. In some embodiments, a target sequence is located in the nucleus or cytoplasm of a cell. In some embodiments, the target sequence is located within an organelle of a eukaryotic cell, for example, mitochondrion or chloroplast.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Examples of Cas proteins include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and homologs or derivatives thereof.

In some embodiments the CRISPR enzyme is Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. Codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence.

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome.

Several commercially available CRISPR/Cas9 systems for gene editing are available in the art. Any such systems, and any variations thereof, can be used in connection with methods provided herein.

In certain aspects, the therapeutic agent targeting the circRNA is an antibody or antigen-binding fragment.

The term "antibody," "immunoglobulin," or "Ig" is used interchangeably herein, and is used in the broadest sense and specifically encompasses, for example, individual anti-circRNA monoclonal antibodies (including agonist, antagonist, neutralizing antibodies, full length or intact monoclonal antibodies), anti-circRNA antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-circRNA antibodies, and fragments of anti-circRNA antibodies, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., Antibody Engineering (Borrebaeck ed., 2d ed. 1995); and Kuby, Immunology (3d ed. 1997). In specific embodiments, the specific molecular antigen (e.g., the circRNA, circRNA junction, etc.) can be bound by an antibody provided herein. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments such as circRNA-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments such as circRNA-binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a circRNA antigen (e.g., one or more CDRs of an anti-circRNA antibody). Such antibody fragments can be found in, for example, Harlow and Lane, Antibodies: A Laboratory Manual (1989); Mol. Biology and Biotechnology: A Comprehensive Desk Reference (Myers ed., 1995); Huston et al., 1993, Cell Biophysics 22:189-224; Plückthun and Skerra, 1989, Meth. Enzymol. 178:497-515; and Day, Advanced Immunochemistry (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule.

In some embodiments, the design of antibody fragments (Fabs) to target a specific circRNA uses phage selection. This process involves assessment of the affinity of antibody fragments to the target sequence of interest and is described in Ye et al., "Synthetic antibodies for specific recognition and crystallization of structured RNA" (2008) PNAS 105 (1):82-87 and Sherman et al., "Specific RNA-Binding Antibodies with a Four-Amino-Acid Code," J. Mol. Biol. (2014) 426, 2145-2157. This approach results in the generation of an antibody library that can be used to target a specific RNA/circRNA.

In certain aspects, binding specificity and affinity can vary depending on the circRNA of interest with Fab design. Dominguez et al., "Sequence, Structure, and Context Preferences of Human RNA Binding Proteins," (2018) Molecular Cell 70, 854-867 reviews and details features and characteristics of human RNA binding proteins.

In some embodiments, up to 20 nucleotides (approximately 10 nucleotides on each side of the circRNA junction) are used as a motif for designing an antibody library against a circRNA. In other embodiments, about 18 nucleotides (approximately 9 nucleotides on each side of the circRNA junction), about 16 nucleotides (approximately 8 nucleotides on each side of the circRNA junction), about 14 nucleotides (approximately 7 nucleotides on each side of the circRNA junction), about 12 nucleotides (approximately 6 nucleotides on each side of the circRNA junction), about 10 nucleotides (approximately 5 nucleotides on each side of the circRNA junction), about 8 nucleotides (approximately 4 nucleotides on each side of the circRNA junction), about 6 nucleotides (approximately 3 nucleotides on each side of the circRNA junction), or about 4 nucleotides (approximately 2 nucleotides on each side of the circRNA junction) are used as a motif for designing an antibody library against a circRNA. In certain aspects, a shorter sequence yields improved specificity and is associated with increased statistical power for higher affinity for binding.

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003); *Therapeutic Monoclonal Antibodies: From Bench to Clinic* (An ed. 2009); *Monoclonal Antibodies: Methods and Protocols* (Albitar ed. 2010); and *Antibody Engineering* Vols 1 and 2 (Kontermann and Dübel eds., 2d ed. 2010).

In another aspect, a process called RNA immunoprecipitation (RIP) is used to pull down circRNAs by using antibodies/proteins. An example of a study using this methodology is described in Wang et al., "Circular RNA FOXP1 promotes tumor progression and Warburg effect in gallbladder cancer by regulating PKLR expression," (2019) Mol Cancer 18, 145. This approach requires having an antibody that is used for targeting a specific RNA/circRNA or knowing what proteins bind a specific RNA/circRNA. In the aforementioned study, identification of proteins that bind a specific circRNA was performed by pulling down RNAs and performing proteomics analyses. RIP is typically used for discovery of RNAs/circRNAs and/or targeted analysis of specific RNAs/circRNAs.

The following examples are given for purely illustrative and non-limiting purposes of the present invention.

EXAMPLES

Example 1. A Non-Limiting Embodiment of ACValidator

Figure 2A:
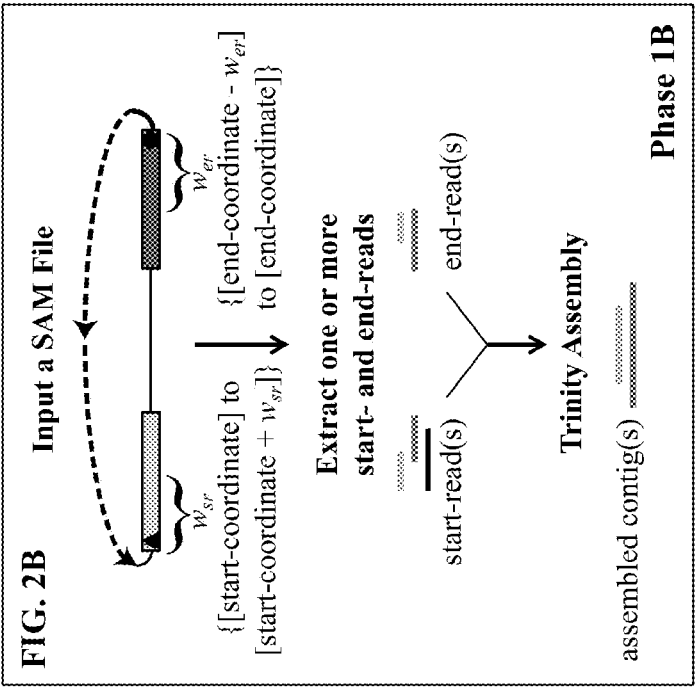
FIGS. 2A, 2B, and 2C depict another non-limiting embodiment of the ACValidator workflow. ACValidator takes as input a circRNA junction coordinate to be validated, a sequence file (e.g., a sequence alignment mapping (SAM) file), and a reference genome.
Figure 2B:
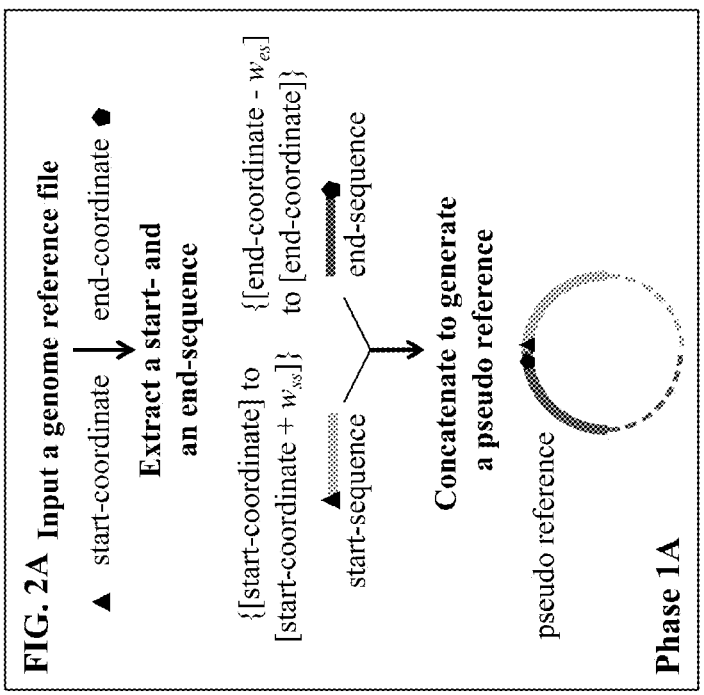
Figure 2C:
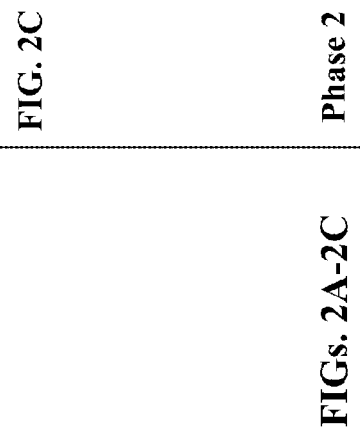

ACValidator receives as inputs, a sequence file of a library (a SAM file), a reference genome, and a circRNA junction coordinate to be validated. The circRNA junction includes an end-coordinate (the splice donor) and a start-coordinate (the splice acceptor). ACValidator includes at least three phases (FIGS. 2A-2C).

In phase 1A (FIG. 2A), reads are extracted from either side of the SAM file using a user-defined window size w. End-reads are within "end-coordinate−w" and "end-coordinate." Start-reads are within "start-coordinate" and "start-coordinate+w." The window size w can be adjusted based on the library insert size (n), read length (m), or both. In one set of experiments, datasets were run using w=300 bp. In another set of experiments, datasets were run using two different window sizes, where w=insert size or w=2*insert size, in order to understand the effect of window size on the results. The above-mentioned window sizes were chosen in order to capture as many reads overlapping the circRNA junction as possible, given the use of paired-end sequencing data. However, a range of values between insert size and 2*insert size can be used, and users can adjust this parameter based on their library insert size.

A software program is used for extracting aligned reads within w bp on either side of the junction from the SAM file. Here, the inventors used SAMtools (Li et al., 2009). The extracted read is converted (e.g., into a FASTQ format), and a contig (e.g., in a FASTA file) is generated using an assembler (e.g., Trinity (Haas et al., 2013)).

In phase 1B (FIG. 2B), a "pseudo-reference" containing the circRNA sequence to be validated is generated from the reference genome. The pseudo-reference consists of w bp from either side of the circRNA junction of interest by extracting w bp from the end and start of the circRNA junction from the genome reference FASTA file (GRCh37) and concatenating the two sequences from end to end to capture the sequence on either side of the circular junction.

In phase 2 (FIG. 2C), the generated contigs (from phase 1A) are aligned to the pseudo-reference (from phase 1B) using a software BWA-MEM to produce an alignment record (Li, 2013). The junction is validated when the overlap between the two sequences is above a user-defined threshold. For example, the minimum length of the alignment regions on either side of the circRNA junction is for high stringency, 30 bp (total 60-bp overlap); for medium stringency, 20 bp (total 40-bp overlap); for low-stringency, 10 bp (total 20-bp overlap); and for very-low-stringency, 5 bp (total 10-bp overlap).

Example 2. Software Requirements/Dependencies

In some embodiments, ACValidator is implemented on a Linux-based high-performance computing cluster and has minimal requirements and dependencies. The requirements include the following: (a) Trinity v2.3.1 or above; (b) Python v2.7.13 or higher with the pysam package installed; and (c) Bowtie2 v2.3.0 (Langmead and Salzberg, 2012) or above; (d) SAMtools v1.4 or above, and (e) BWA v0.7.12 or above.

Example 3. Computational Cost Overview

Evaluations were run on a linux-based high-performance computing cluster running CentOS version 7. The computational cost of ACValidator directly correlates with the number of reads in the input sample. The only rate-limiting step in using ACValidator is read alignment to generate the SAM file, which is performed prior to starting the workflow. The python validation script following this step requires less than two minutes of runtime for one sorted BAM file of approximately 8 GB, thus making this invention highly computationally efficient.

Example 4. Validation of ACValidator Using Simulated Datasets

To evaluate ACValidator, nine simulation datasets with varying circular, linear RNA coverages, and read lengths were generated (Table 1A). Since highly expressed circRNAs are more often of interest, the top 100 most highly expressed circRNAs from each dataset were evaluated, similar to a previous study (Hansen, et al., 2016). 100 random non-circRNA coordinates as false positive candidates from each dataset were selected.

Figure 3:
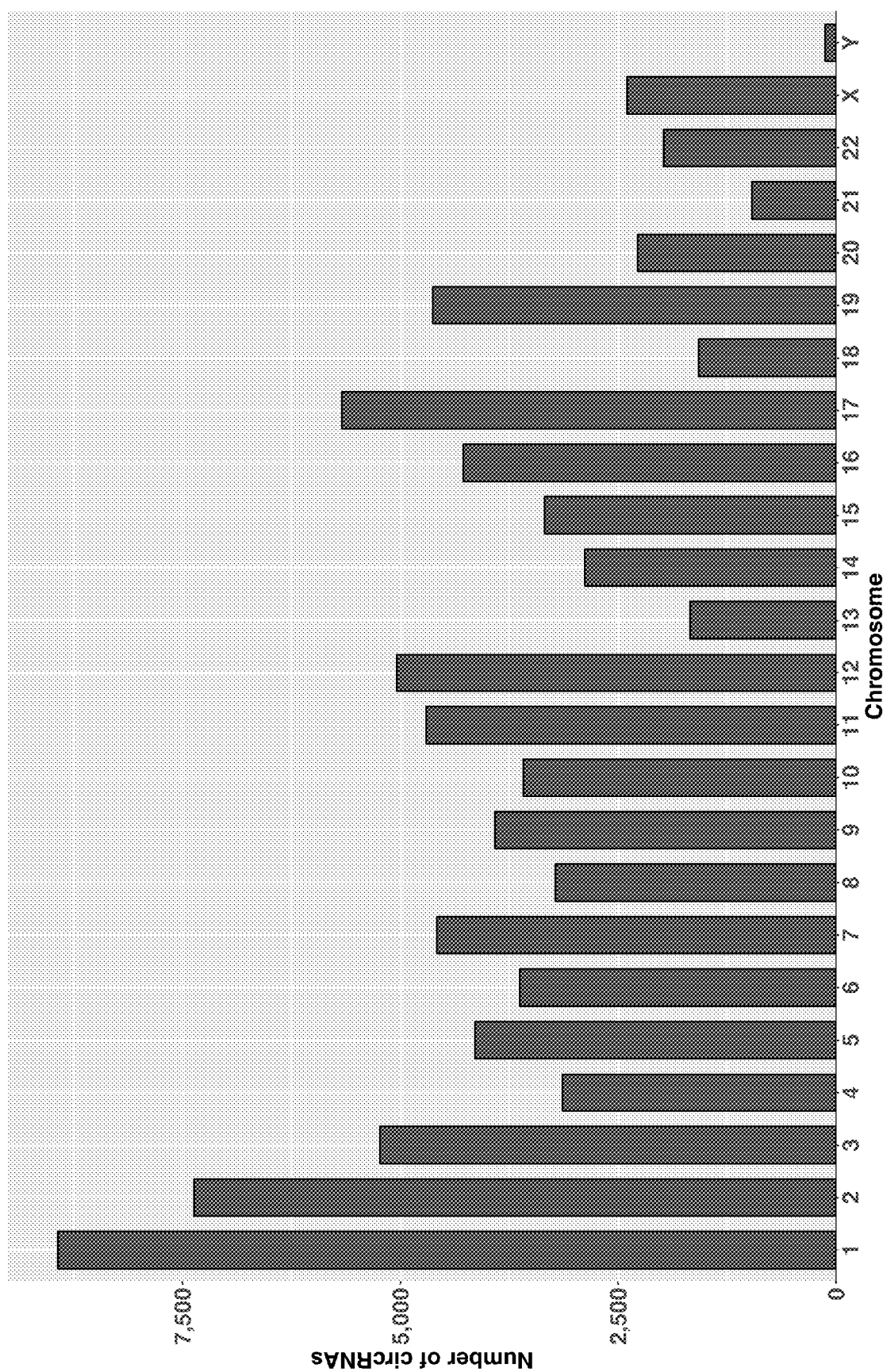
FIG. 3 depicts the chromosomal distribution of simulated datasets. Simulation datasets were generated using CIRI-simulator, which ensures circRNAs are simulated across all chromosomes. The distribution of generated circRNAs across the different chromosomes is similar to the chromosomal size distribution

CIRI-simulator (Gao et al., 2015) was used to generate nine synthetic RNA-Seq datasets that had varying coverage of circular and linear RNA (Table 1A) to evaluate workflows. CIRI-simulator takes a FASTA-formatted reference file and a GTF annotation file as input and generates circular and linear RNA sequences. Recently, CIRI-simulator is re-designed (Zeng et al., 2017) to generate synthetic reads for circRNAs deposited in circBase (Glazar et al., 2014). Simulated datasets with 2-24 supporting reads, a minimum circRNA size of at least 50 bp, and an insert size of 300 bp were generated. Overall, there was an average of 89,293 circRNAs across these nine simulated datasets. CIRI-simulator ensures these circRNAs mapped to locations distributed across the entire genome, thereby eliminating any bias associated with the genomic location (FIG. 3).

The nine simulation datasets have variable supporting reads (2-24 supporting reads in total, with an average number of 2-10) for circular and linear RNAs, as well as three different read lengths (50, 100, 150 bp) to evaluate the performance of our workflow (Table 1A). The top 100 most highly expressed circRNAs from each dataset were used as true positives. 100 randomly selected non-circRNA coordinates were used as false positive candidates. CIRI-simulator ensures these circRNAs map to locations distributed across the entire genome, thereby eliminating any bias associated with genomic location (FIG. 3). The generated true positive simulation datasets are named using the convention: pos_<circRNA_coverage>_<linearRNA_coverage>_<read_length> (pos: positive; Table 1A).

Figure 4A:
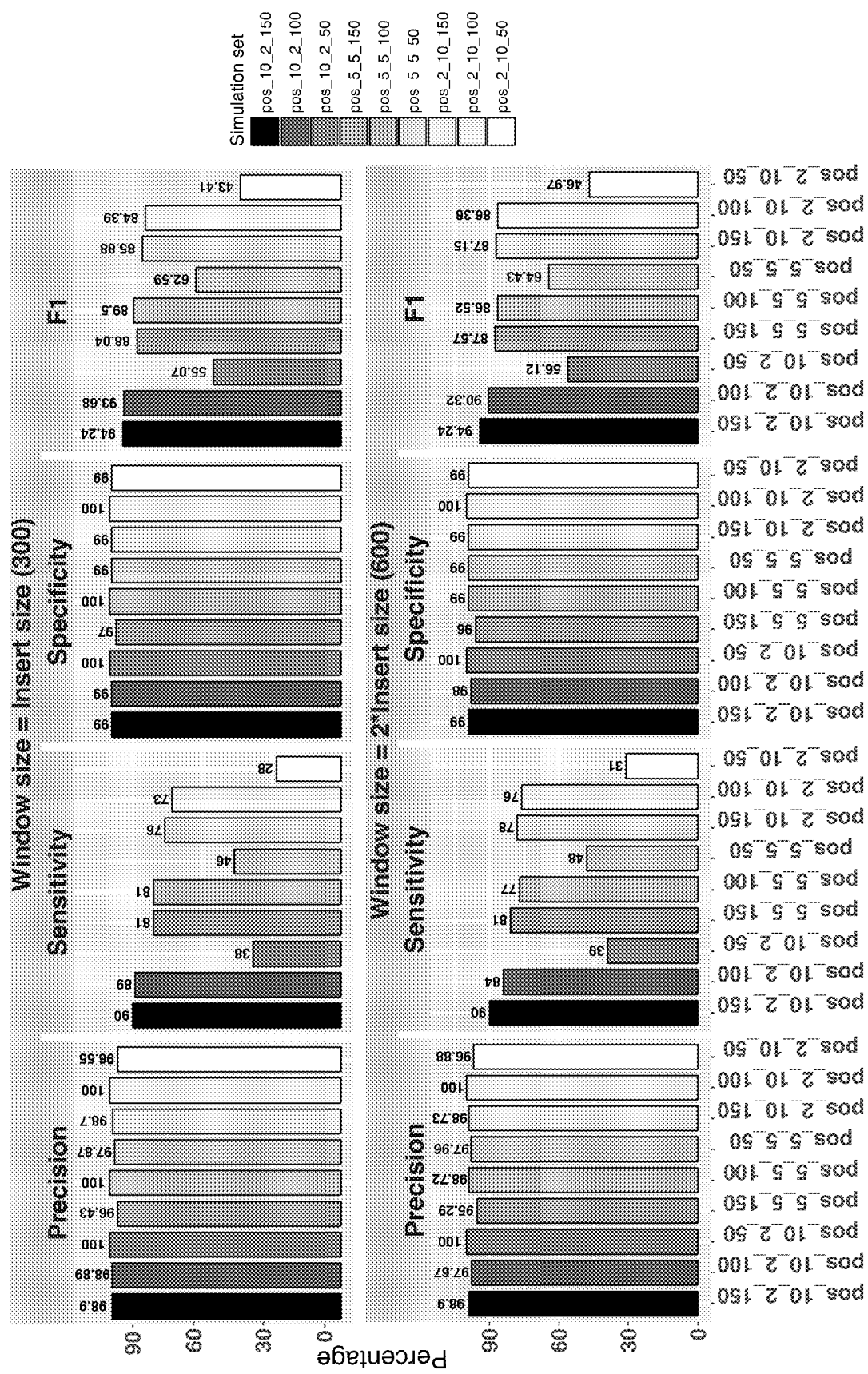
FIG. 4A depicts performance of ACValidator on simulated datasets described in Table 1A. The 100 candidate circRNA junctions with the highest number of supporting reads were considered true positive (TP). The 100 randomly selected non-circRNA junction coordinates were considered true negative (TN). The simulation datasets are described in Table 1A and each simulation dataset (x-axis) is named using the naming convention: pos_<circRNA_coverage>_<linearRNA_coverage>_<read_length> (pos: positive). The panels represent ACValidator performance on top 100 TP candidates using a) window size=insert size (300 bp) and b) window size=2*insert size (600 bp).

To understand the effect of the user defined parameter window size w on the results, the analysis was replicated using two different window sizes: 1) w=insert size (300 bp) 2) w=2*insert size (600 bp). It was observed that simulations with higher circRNA coverages, longer read lengths, or both achieved higher sensitivity (FIG. 4). Specifically, when using w=300, simulations 1 and 2, which have the highest circRNA coverage (10) and read lengths (150, 100 bp respectively) achieved the highest sensitivity of 90% and 89%, respectively. However, for simulation 3 where the read length was only 50 bp, the sensitivity fell to 38%. As the circRNA coverage decreases, the sensitivity also gradually reduces to 81% and below, with a further reduction in sensitivity to 46% and 28% observed for datasets with shorter read lengths (simulations 6 and 9). In datasets with lower circRNA coverage, shorter read length, or both, this reduction in sensitivity was because Trinity did not find sufficient reads to assemble across these regions and hence was not able to generate contigs. A similar pattern was detected when using w=600, and a drastic difference in sensitivity between the two window sizes was not observed. Further, the F1 score [F1=(2*Precision*Sensitivity)/(Precision+Sensitivity)], a measure of accuracy, which indicates how well a tool achieves sensitivity and precision simultaneously, was calculated (FIG. 4). The results were found to be consistent with sensitivity measurements, indicating that higher circRNA coverage coupled with longer read length yields better performance using our methods.

Figure 5A:
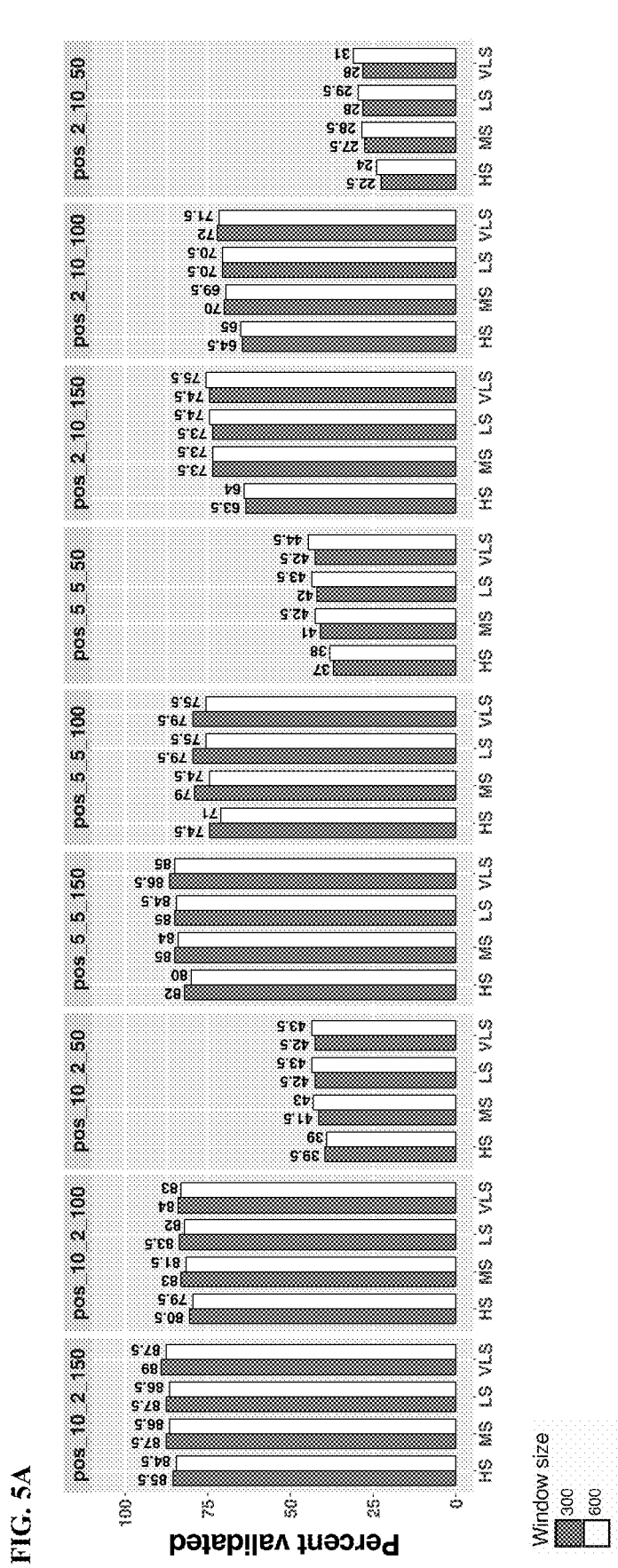
FIGS. 5A and 5B depict performance of ACValidator evaluated with two different window sizes, 300 and 600 bp.
Figure 5B:
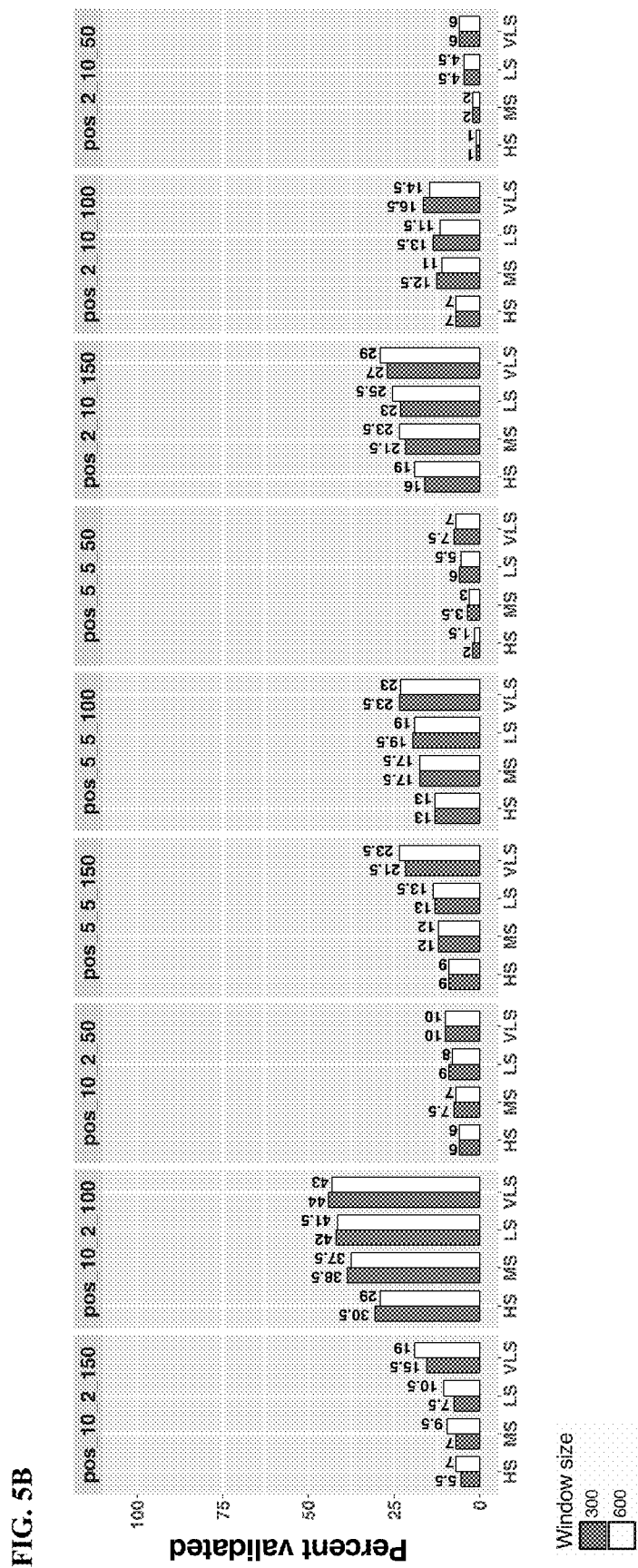

The analysis was extended to the top 200 most highly expressed as well as bottom 200 least expressed candidates, and a similar trend in performance was observed (FIG. 5). Additionally, sensitivity was evaluated using four stringency thresholds for the number of overlapping bases (30 bp, 20 bp, 10 bp, and 5 bp) to assess whether saturation in sensitivity measurements was achieved. For the top 200 highly expressed circRNAs, sensitivity of over 80% was achieved for simulation datasets 1 and 2, which had the highest circRNA coverage (10) and read lengths (150 and 100), using both window sizes (300 and 600). However, a notable difference was not observed in the number of validations across the different thresholds for the number of overlapping bases, with an average of 86.8% validation for simulation set 1 (pos_10_2_150), 71.5% validation for simulation set 7 (pos_2_10_150), and 27.3% validation for simulation set 9 (pos_2_10_50; FIG. 5A). For the bottom 200 least expressed candidates, lower stringency criteria resulted in more validations than the higher stringency criteria, with an average of 19.3% and 10.1% validation for the very low and high stringencies respectively. The overall validation percentages were below 45% across all the simulation datasets for these bottom 200 circRNA candidates (FIG. 5B).

Example 5. Validation of ACValidator Using Experimental, Non-Simulated Datasets

To test ACValidator on experimental data, six pairs of ribonuclease R (RNase R)-treated and non-treated samples (N=12, Table 2) were analyzed. RNase R is widely used for circRNA enrichment because it is an exoribonuclease that selectively digests linear RNA but leaves behind circular structures. Three of the sample pairs were downloaded from the sequence read archive (SRA) (Leinonen et al., 2011) and generated from HeLa and Hs68 cell lines with or without RNase R treatment. The remaining three sample pairs were generated in-house from total RNA extracted from the middle temporal gyms (MG) of three healthy elderly control brains. All data generated through this study are accessible through the European Genome Archive (EGA; accession EGAS00001003128).

ACValidator was evaluated using experimental, non-simulated datasets generated from tissues or cell lines (Table 2). Since the true positive circRNAs for these datasets are not known, ACValidator on the circRNAs that were called in both the RNase R-treated and non-treated datasets using six existing circRNA detection algorithms, find_circ, CIRI, Mapsplice, KNIFE, DCC, and CIRCexplorer. Specifically, a candidate was considered a true circRNA if it was called by at least three of the six tools in both the treated and non-treated samples, and was not depleted following RNase R enrichment. A circRNA candidate is determined to be not depleted if the spliced reads per billion mapping (SRPBM) value does not decrease following the enrichment. ACValidator was run on the non-depleted potential true circRNA candidates for evaluation.

Figure 6:
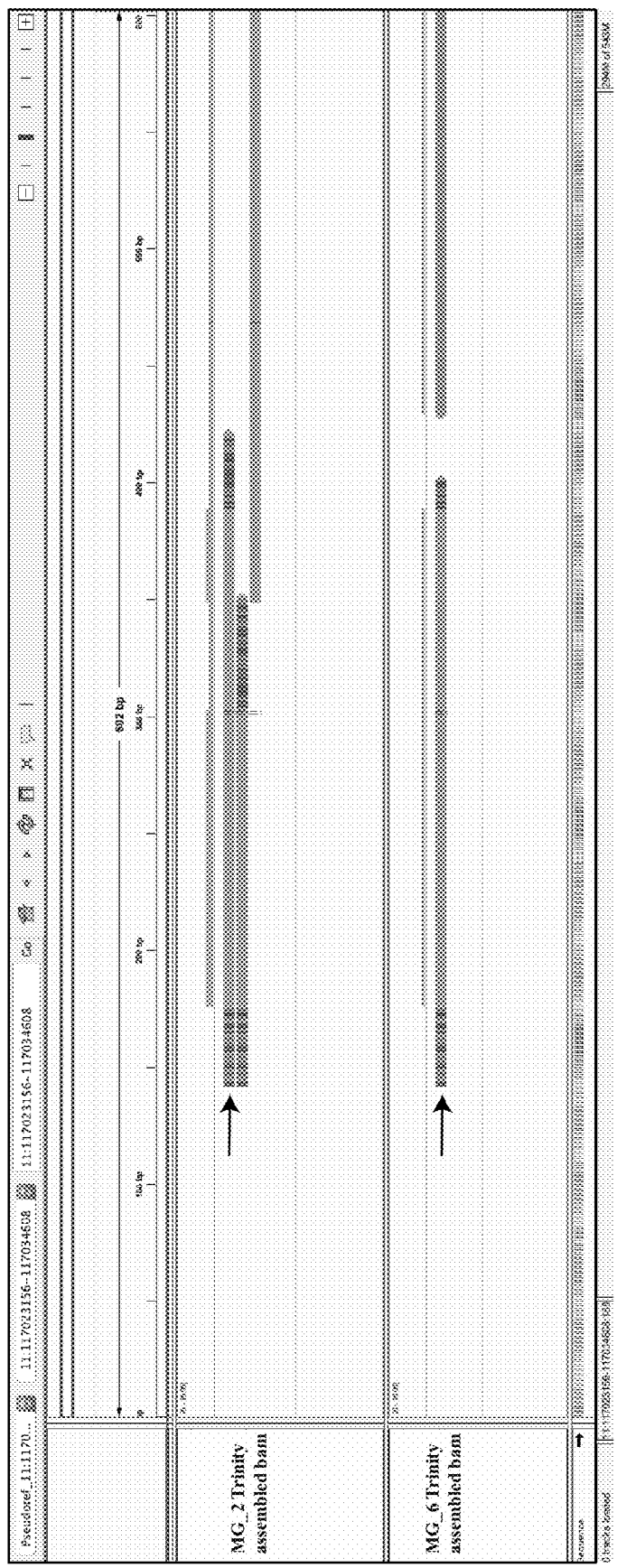
FIG. 6 depicts an integrated genomics viewer (IGV) screen shot of a circRNA candidate (chr11:117,023,156-117,034,608) a) assembled contigs generated by ACValidator on RNase R-treated (top panel) and non-treated (bottom panel) human middle temporal gyms (MG) samples, aligned to the corresponding pseudo-reference. This circRNA was detected in both the treated and non-treated samples by at least three of the six existing circRNA prediction algorithms, and was not depleted following RNase R treatment. The circRNA junction of interest is at 300 bp, and pink bars that span over this junction represent the contigs that validate the junction (colored segments at the ends of contigs represent soft-clipped bases; arrows indicate the generated contigs that overlap with the circRNA junction). Reads from these samples aligned to the reference are shown in FIG. 7.
Figure 7:
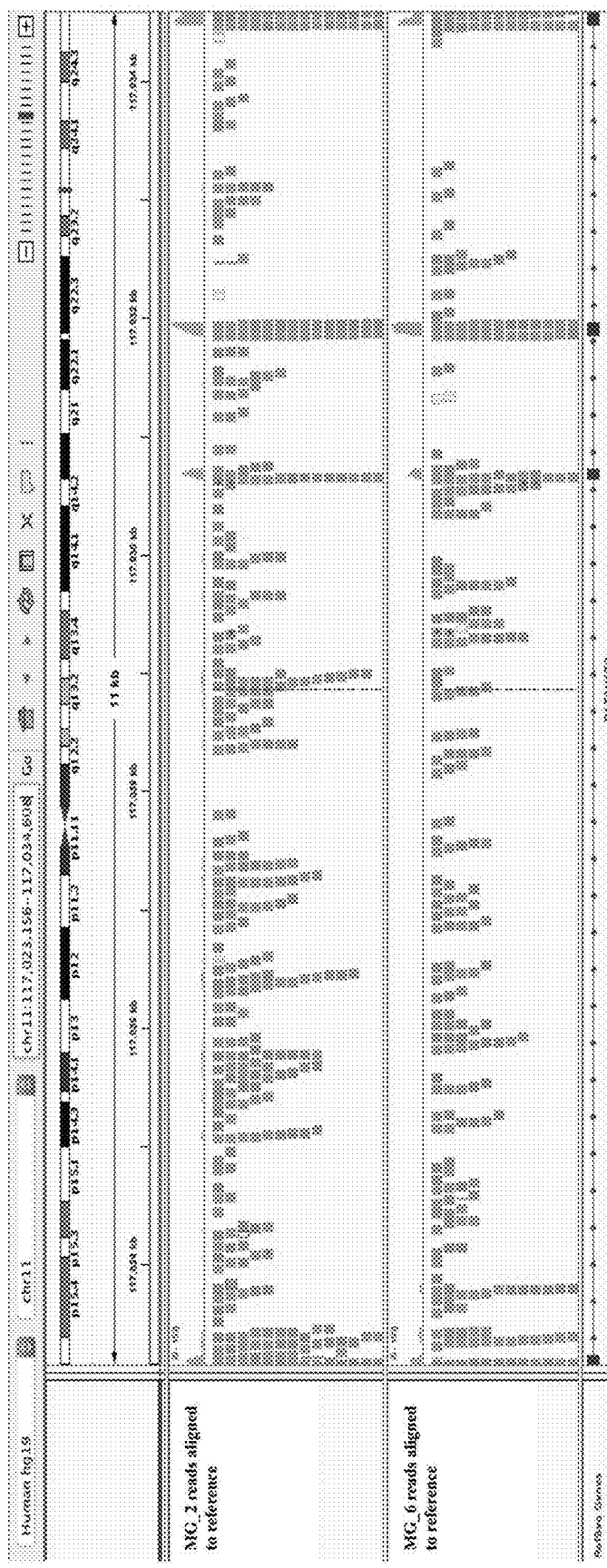
FIG. 7 depicts reads from the RNase R-treated (top panel) and non-treated (bottom panel) MG samples MG_2 and MG_6 respectively, aligned to the human reference genome (hg19).

Overall, except for the SRR1636986-SRR1637090 pair, over 89% of the candidates that were called in both the treated and non-treated pairs were not depleted (i.e., SRPBM after RNase R treatment>SRPBM prior to treatment). Among these non-depleted candidates, ACValidator was able to construct contigs spanning the circRNA junction for more than 75% of them for the RNase R-treated samples and 47-57% of them for the non-treated samples using the medium-stringency criteria and both the window sizes (Table 3). This increased validation rate for the treated samples is expected since RNase R treatment enriches for circRNAs and hence a higher number of back-splice junction supporting reads was observed. Further, higher numbers of validated circRNAs were detected using lower stringency cut-offs for alignment overlap between contigs and junction sequences (Table 3). As observed in the simulation datasets, the different window sizes did not notably affect the number of validations among these experimental datasets (Table 3). FIG. 6 shows an example of a circRNA (Jeck, et al., 2013; Salzman, et al., 2013) that was validated by ACValidator in an MG treated and non-treated pair (reads from this sample aligning to the reference are shown in FIG. 7).

The goal of ACValidator is to narrow down a list of potential high-confidence circRNAs. To further evaluate the utility of our methods, the results from each individual tool to those from ACValidator were compared. For this analysis, the top 100 most highly expressed candidates from among those the inventors considered as true positives for these experimental datasets were used (called by at least three of six tools, in both treated and non-treated samples, and SRPBM after RNase R treatment>SRPBM before treatment). Among the in-house treated MG samples, except for CIRCexplorer and Mapsplice, ACValidator was able to in-silico validate a higher number of circRNAs, using medium stringency criteria (20 bp overlap on either side of circRNA junction), than was detected individually by the other tools (Table 4). Among the SRA samples however, our methods validated a fewer number of circRNAs than were detected by individual tools except find_circ. Thus, results may vary depending on which individual tool is used for circRNA detection.

Example 6. Validation Using Polymerase Chain Reaction (PCR)

In some embodiments, PCR is performed to experimentally validate the circRNA candidate that is in silico validated by ACValidator. RNA is isolated from a tissue sample, for example, MG of three postmortem tissue samples. cDNA is synthesized from the RNA using reverse transcriptase. For example, from about 500 ng of the RNA using SuperScript II reverse transcriptase (ThermoFisher Scientific, Waltham, MA). PCR was performed using 100 ng cDNA of each sample, 12.5 µL of Kapa HiFi polymerase (2×), 1 µL of the forward primer (5 µM), 1 µL of the reverse primer (5 µM), and 9.54 µL of molecular-grade water with the following thermocycler program: denaturation—60 seconds at 95° C., amplification—15 seconds at 95° C., 15 seconds at 55-63° C., 30 seconds at 72° C. (cycle 35-40×), extension—60 seconds at 72° C.

A PCR primer set is designed (e.g., using Primer3 (Untergasser et al., 2012; Koressaar & Remm, 2007; http://bioinfo.ut.ee/primer3-0.4.0/)) to target the flanking exons of the candidate circRNA junction site, and the PCR product size is assessed, for example, on a TapeStation 4200 instrument (Agilent Technologies, Santa Clara, CA).

The selected circRNA candidates, in silico validated by ACValidator and detected by all six existing tools in each sample, were experimentally validated. Since each treated-non-treated pair is generated from the same donor, validations were run on the non-RNase R treated cDNA from each donor. For three of the candidates, results of ACValidator correlated with those of the experimental validation (FIG.

8). For candidate chr10:116,879,948-116,931,050, ACValidator was able to validate the junction in two of the three samples, while chr9:113734352-113735838 and chr5:38,523,520-38,530,768 were validated in all three samples using all the stringency cut-offs.

ACValidator, a novel bioinformatics workflow, can be used to validate circRNA candidates of interest in silico and thus helps to identify true positive candidates. In certain aspects, this workflow applies to polyA-selected dataset, polyA-non-selected RNA-Seq dataset, or both, and can be used as a complementary/orthogonal strategy to validate circRNAs from various sample types and diseases. When different circRNA detection algorithms identify different circRNA candidates, ACValidator can be used to narrow down specific candidates of interest. Further, ACValidator can also serve as a circRNA candidate selection tool for experimental validations or functional studies.

When evaluated on simulated datasets, ACValidator achieves improved performance when higher numbers of circRNA supporting reads and longer read lengths are available. Thus, coverage as well as read length are important factors contributing to the performance of ACValidator, since a higher number of reads as well as longer read lengths result in improved assembly. When tested on circRNA candidates that were not depleted between RNase R-treated and non-treated sample pairs, a higher validation rate in treated samples was observed.

Window size, the region from where reads are extracted for assembly, is an important parameter for this approach. Through testing of two different window sizes, one equal to and one twice the insert size, the inventors did not observe notable differences in the number of validations. Additionally, the inventors applied different stringency thresholds based on the extent of contig alignment, but the inventors did not observe notable differences in the number of validated candidates across the different thresholds for highly expressed candidates.

Example 7. Additional Performance Evaluation of ACValidator

The inventors used CIRI-simulator to generate 18 synthetic RNAseq datasets that had variable average number of supporting reads for circular and linear RNAs (2-80), as well as three different read lengths (50, 100, 150 bp) to evaluate the performance of our workflow (Table 1). CIRI-simulator takes a FASTA-formatted reference file and a GTF annotation file as input, and generates circular and linear RNA sequences. Recently, Zeng et al. re-designed this tool to generate synthetic reads for circRNAs deposited in circBase. The inventors generated simulated datasets with minimum circRNA size of at least 50 bp and insert size of 300 bp. Overall, an average of 89,293 circRNAs was generated across these simulated datasets. CIRI-simulator ensures these circRNAs map to locations distributed across the entire genome, thereby eliminating any bias associated with genomic location (FIG. 2). The generated true positive simulation datasets are named using the convention pos_<circRNA_coverage>_<linearRNA_coverage>_<read_length> (pos: positive; Table 1).

To evaluate ACValidator, the inventors generated 18 simulation datasets with varying circular, linear RNA coverages and read lengths (Table 1B). The inventors selected circRNA candidates above/below an expression cut-off as true positives/true negatives respectively. For true positive candidate set, the inventors selected the top 2% of circRNAs based on supporting read counts (expression level) while for the true negative candidate set, the inventors selected the bottom 1% of circRNAs, also based on the supporting read counts (Table 1B). The inventors replicated the analysis using two different window sizes: 1) w=insert size (300 bp) 2) w=2*insert size (600 bp).

Figure 4B:
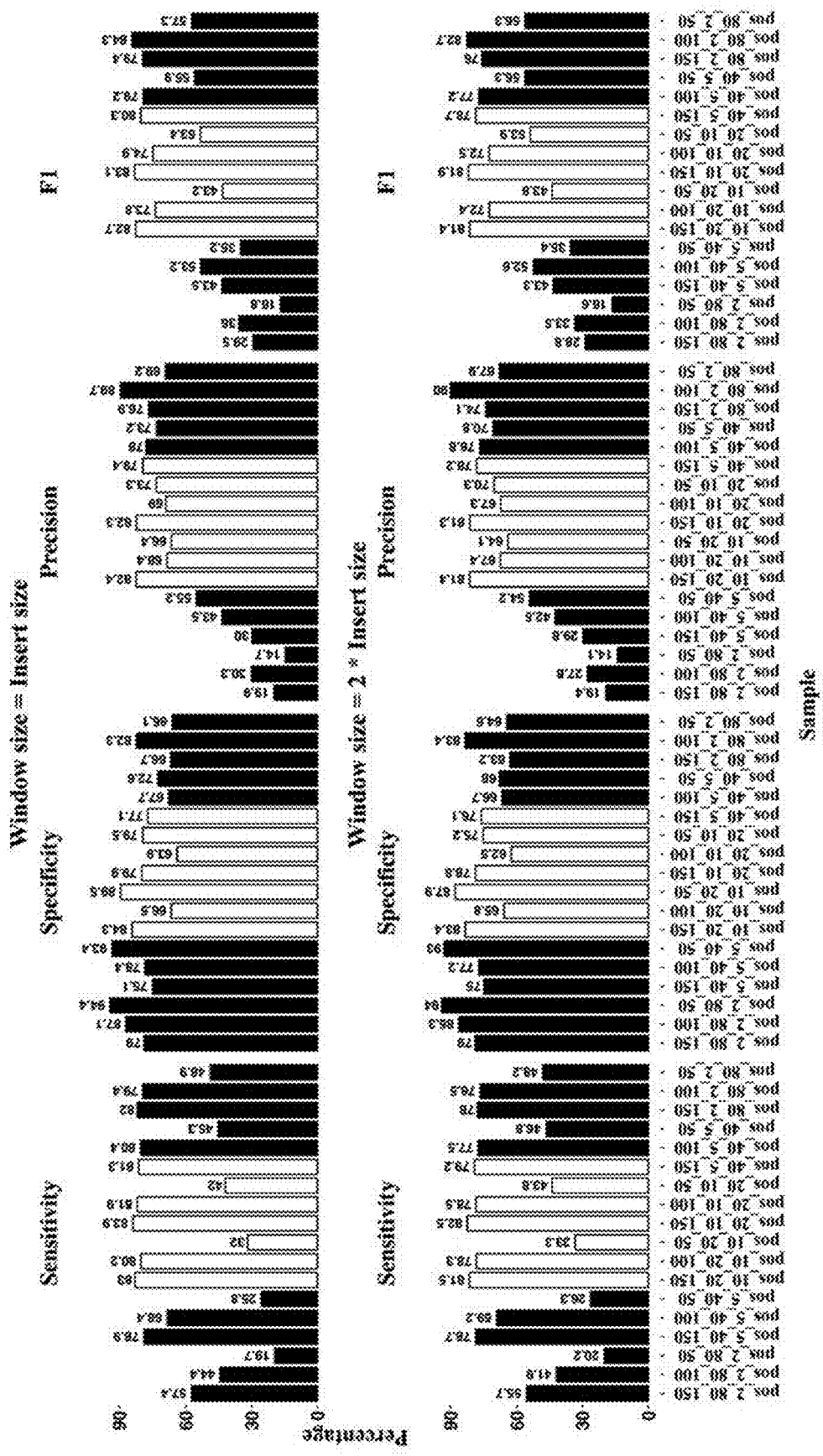
FIG. 4B depicts ACValidator performance on true positive and true negative circRNA candidates from simulated datasets. The top 2% of circRNA candidates based on the number of supporting reads were considered true positives (TP) and the bottom 1% of circRNA candidates based on the number of supporting reads were considered true negatives (TN). The simulation datasets are described in Table 1B and each simulation dataset (x-axis) is named using the following naming convention: pos_<circRNA_coverage>_<linearRNA_coverage>_<read_length> (pos: positive). The panels represent ACValidator performance on TP and TN candidates when using an overlap cut-off of 10 bp between the contig and pseudo-reference, and a) window size=insert size (300 bp) and b) window size=2*insert size (600 bp). P=TP/(TP+FP); S=TP/(TP+FN); Sp=TN/(TN+FP); F1=(2*P*S)/(P+S). FP, false positives; FN, false negatives; S, sensitivity; Sp, specificity; P, precision.

The inventors observed that simulations with higher circRNA coverages and longer read lengths achieved higher sensitivity (FIG. 4B). Specifically, when using w=300 and overlap cut-off of 10 bp between the contig and pseudo-reference, simulations 7, 10, 13 and 16, which have average circRNA coverages greater than 10 and read length of 150 bp achieved over 81% sensitivity. For simulations 8, 11, 14, and 17, for which the average circRNA coverage was greater than 10 but the read length was reduced to 100 bp, the inventors observed a slight reduction in sensitivity of by approximately 1-3 percentage points. However, when further reducing the read length to 50 bp, the sensitivity reduced to <=49% for simulations 9, 12, 15 and 18 (average circRNA coverage>10). When the average circRNA coverage was decreased to 5 or below (simulations 1-6), the inventors observe an overall reduction in sensitivity while datasets with longer read lengths demonstrated improved performance compared to ones with shorter read lengths (20-26% sensitivity for simulations 3 and 6 and 57-79% for simulations 1 and 4, respectively). In datasets with lower circRNA coverage and/or shorter read length, this reduction in sensitivity was because Trinity did not find sufficient reads to assemble across these regions and hence was not able to generate contigs. The inventors detect a similar pattern when using w=600 and did not observe a drastic difference in sensitivity between the two window sizes. Further, the inventors calculated the F1 score [F1=(2*Precision*Sensitivity)/(Precision+Sensitivity)], a measure of accuracy, which indicates how well a tool achieves sensitivity and precision simultaneously (FIG. 4B). The inventors observed that for datasets with read length of 100 bp, the F1 score increases with coverage, while for datasets with read length of 150 bp, a saturation is attained for datasets with average circRNA coverage above 20. Overall, results from our simulation data indicates that higher circRNA coverage coupled with longer read length yields better performance of our approach.

Figure 5C:
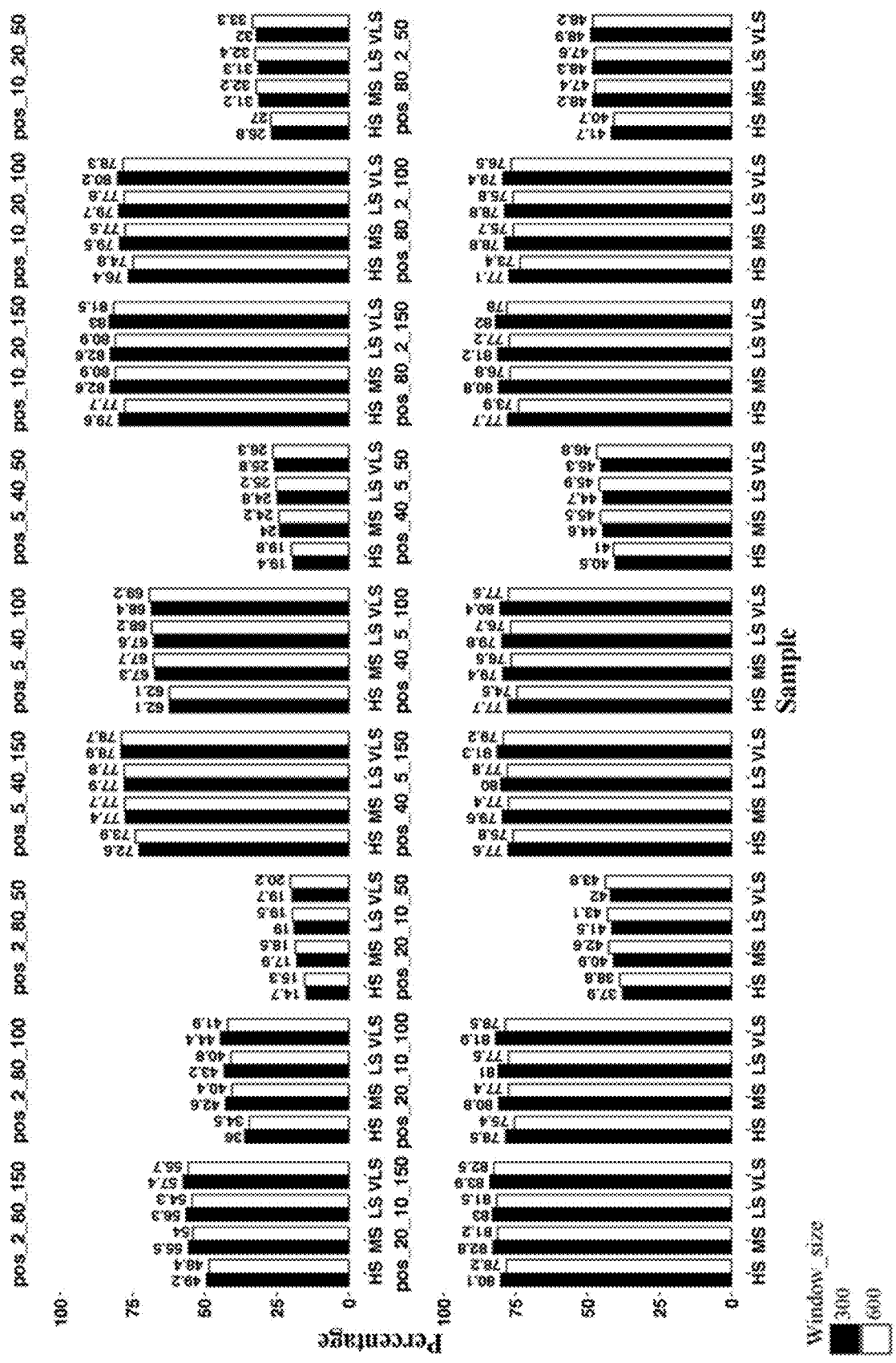
FIG. 5C depicts ACValidator performance across different overlap stringency thresholds in simulated datasets. Sensitivity measurements based on the top 2% of true positive candidates were evaluated across four different overlap stringency thresholds (60, 40, 20 and 10 bp), as well as two different window sizes (300 and 600 bp). HS: high stringency; MS: medium stringency; LS: low stringency; and VLS: very low stringency.

Additionally, the inventors evaluated sensitivity using four stringency thresholds for the number of overlapping bases (30 bp, 20 bp, 10 bp and 5 bp; section: Design and implementation). The inventors observed that for datasets with average circRNA coverage greater than 10 and read lengths 100 or 150 bp, there was no notable difference in the sensitivity across the different thresholds for the number of overlapping bases, with an average of 79-81% sensitivity respectively (FIG. 5C). However, for simulations with circRNA coverage less than 10 and read length of 50 bp, the sensitivity increases by about 4-8 percentage points (10-34%) when reducing the overlap stringency from high to very low (FIG. 5C). Thus, users can choose a less stringent overlap threshold such as 10 bp when running ACValidator on low coverage/short read length datasets but for higher circRNA coverage and longer read lengths, this threshold can be increased to 40 or 60 bp.

Example 8. Experimental Validation of Identified circRNAs

Figure 8A:
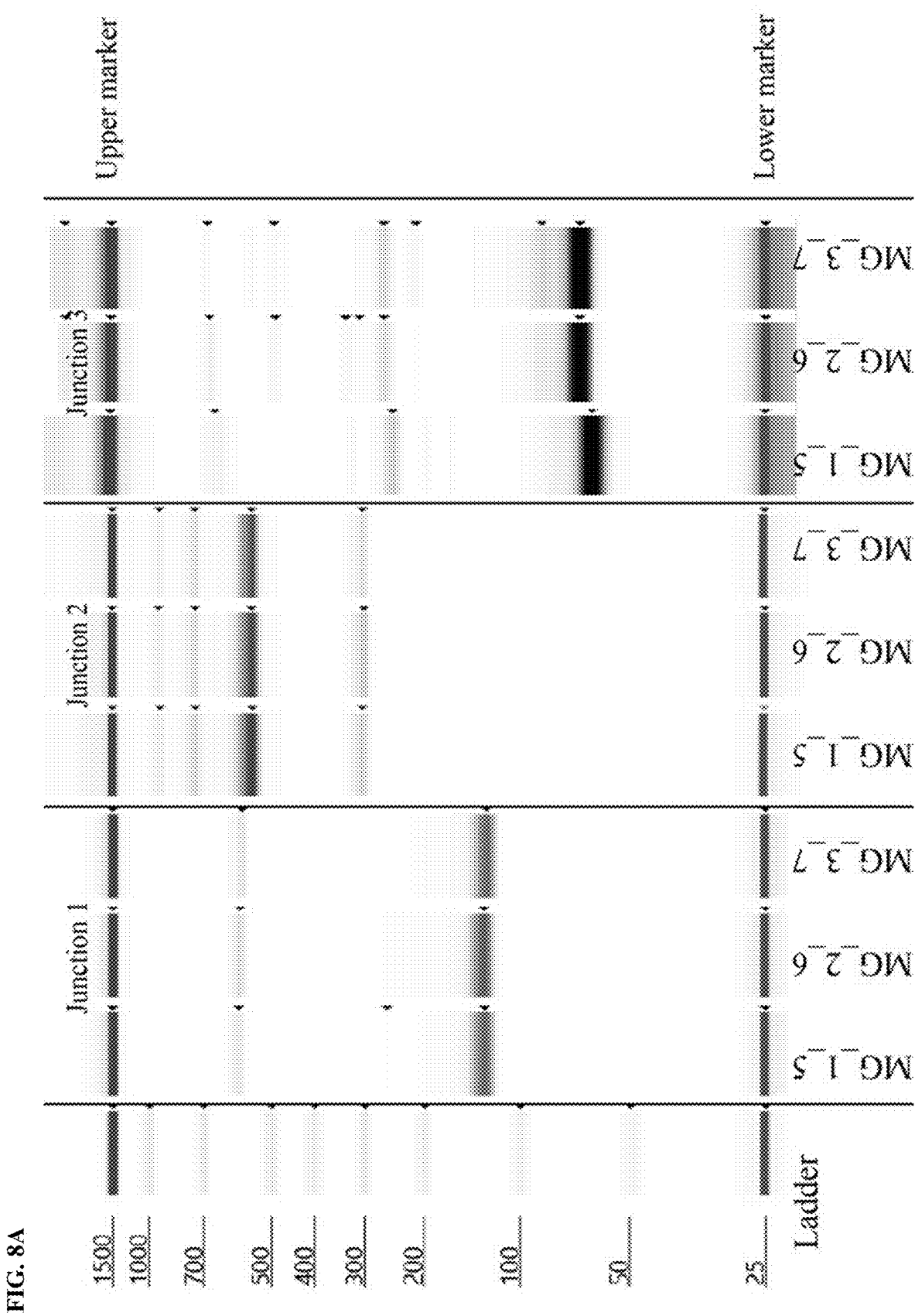
FIG. 8A depicts PCR validation of selected circRNA candidates. The selected circRNA candidates that were validated by ACValidator and detected by all the six algorithms were selected for validation. Among these, ACValidator was able to validate chr10:116,879,948-116,931,050 in two of the three samples, and chr9:113,734,352-113,735,838 and chr5:38,523,520-38,530,768 in all three samples. The remaining two candidates did not validate in our PCR experiments. Left panel: PCR of chr5:38,523,520-38,530,768 (junction 1), expected product size: 130 bp; middle panel: PCR of chr10:116,879,948-116,931,050 (junction 2), expected product size: 679 bp; right panel: PCR of chr9:113,734,352-113,735,838 (junction 3), expected product size: 76 bp.
Figure 8B:
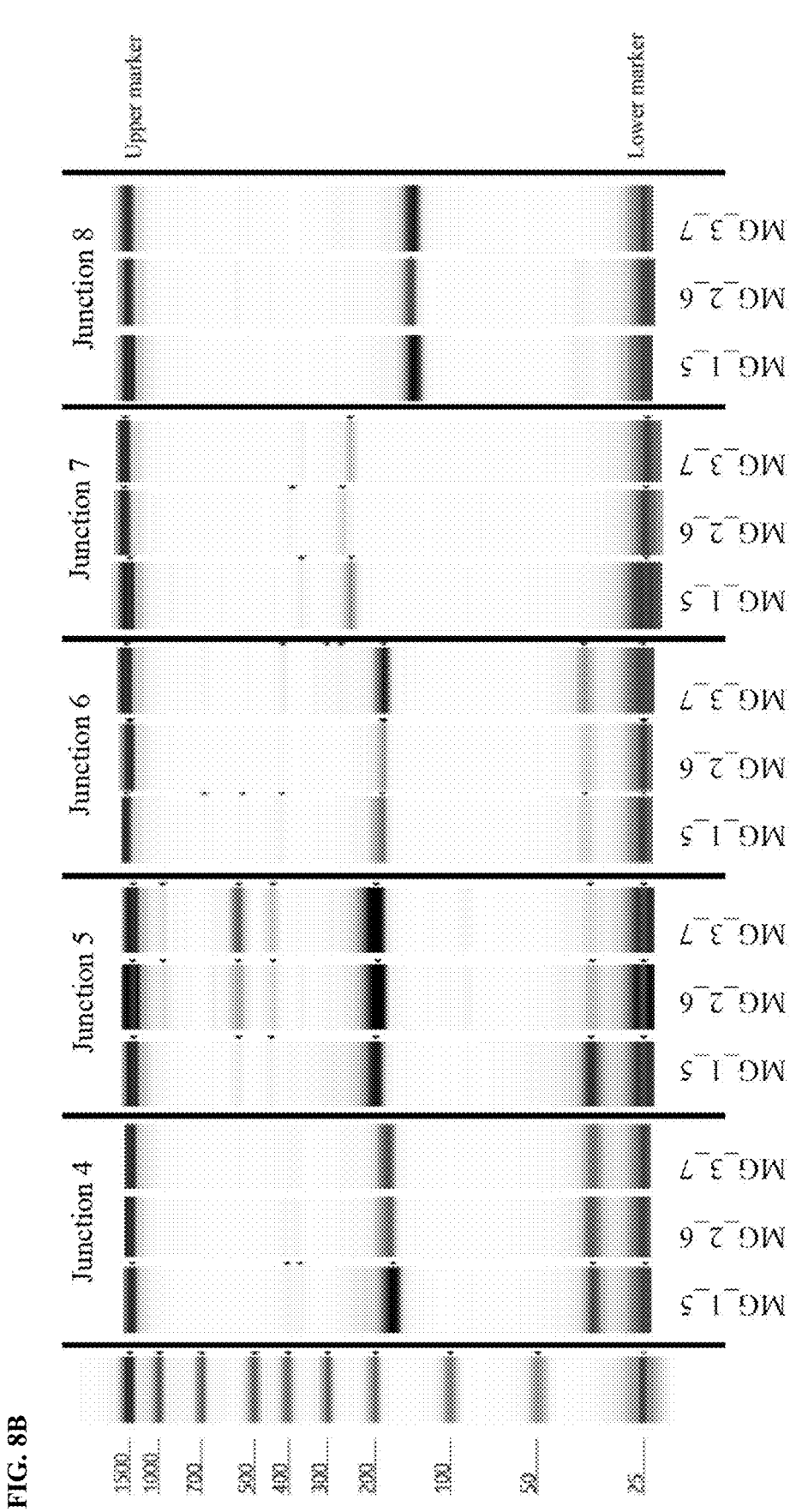
FIG. 8B depicts PCR validation of selected medium expressed circRNA candidates. Five medium expressed circRNAs candidates (600>average SRPBM>300) that were validated by ACValidator and that were detected by three of six algorithms were selected for validation. All circRNAs junctions were validated across the three untreated MG samples. AGILENT TAPESTATION® gel traces are shown. Validated circRNAs include chr5:10,415,599-10,417,516 (junction 4), expected product size: 183 bp; chr7:8,257,934-8,275,635 (junction 5), expected product size: 208 bp; chr5:64,084,777-64,100,213 (junction 6), expected product size: 195 bp; chr4:56,277,780-56,284,152 (junction 7), expected product size: 248 bp; and chr8:37,623,043-37,623,873 (junction 8), expected product size: 154 bp.

Experimental validations were performed for six highly expressed circRNA candidates (average SRPBM>650) that were in silico validated by ACValidator and that were detected by all six tools in each sample. Since the inventors were interested in validating the presence of the circRNA and not their abundance, the inventors performed PCR validations on these selected candidates. Each of the treated-non-treated pair is generated from the same donor and hence, the inventors ran validations on the non-RNase R treated cDNA from each donor. For three of the candidates, ACValidator results were experimentally validated (FIGS. 8A and 8B).

For the candidate circRNA at chr10:116,879,948-116,931,050, ACValidator validated the circRNA junction in two of three samples, while chr9:113,734,352-113,735,838, chr5:38,523,520-38,530,768 and chr8:37,623,043-37,623,873 were validated in all three samples using all stringency cut-offs. For the remaining two candidates, the inventors observed evidence of validation but because differently sized PCR products were generated, the inventors could not determine the exact product size although it is possible that multiple circRNA species may be present.

Additional PCR validations were performed on four circRNAs candidates demonstrating medium expression (average SRPBM>300 and <600), that were validated by ACValidator, and that were called by at least three of six tools. These candidates include chr5:10,415,599-10,417,516, chr7:8,257,934-8,275,635, chr5:64,084,777-64,100,213 and chr4:56,277,780-56,284,152. All junctions were validated across the three untreated MG samples. PCR validations were also performed on two circRNAs candidates demonstrating low expression (average SRPBM<90), that were validated by ACValidator, and that were called by three of six tools. These candidates include chr15:93,540,186-93,545,547 and chr3:3,178,943-3,186,394, and were validated across the three untreated MG samples. Sanger sequencing was also performed on the seven circRNAs candidates demonstrating medium or low expression, and although high background was observed for a large proportion of the reactions, three of the seven candidates were validated in at least one sample. These include junction 6 (for samples MG_1_5 and MG_3_7), junction 8 (for samples MG_2_6 and MG_3_7), and junction 9 (for sample MG_3_7).

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

Table 1A

Simulation dataset parameters with 9 datasets.

| Simulation Data Set | | Average # supporting reads | | Read length (bp) | Insert Size | # of reads generated | Window Lengths Tested (bp) | # of overlapping base thresholds tested |
|---|---|---|---|---|---|---|---|---|
| No. | Name | Circ RNA | linear RNA | | | | | |
| 1 | pos_10_2_150 | 10 | 2 | 150 | 300 | 18,768,200 | 300, 600 | 60, 40, 20, 10 |
| 2 | pos_10_2_100 | 10 | 2 | 100 | 300 | 28,024,890 | 300, 600 | 60, 40, 20, 10 |
| 3 | pos_10_2_50 | 10 | 2 | 50 | 300 | 55,794,356 | 300, 600 | 60, 40, 20, 10 |
| 4 | pos_5_5_150 | 5 | 5 | 150 | 300 | 10,867,166 | 300, 600 | 60, 40, 20, 10 |
| 5 | pos_5_5_100 | 5 | 5 | 100 | 300 | 16,173,002 | 300, 600 | 60, 40, 20, 10 |
| 6 | pos_5_5_50 | 5 | 5 | 50 | 300 | 32,090,962 | 300, 600 | 60, 40, 20, 10 |
| 7 | pos_2_10_150 | 2 | 10 | 150 | 300 | 7,209,692 | 300, 600 | 60, 40, 20, 10 |
| 8 | pos_2_10_100 | 2 | 10 | 100 | 300 | 10,688,368 | 300, 600 | 60, 40, 20, 10 |
| 9 | pos_2_10_50 | 2 | 10 | 50 | 300 | 21,121,578 | 300, 600 | 60, 40, 20, 10 |

* All simulation datasets based on data generated from human cerebellum and diencephalon, SH-SY5Y cells, Hs68 cells, HeLa cells, and HEK293 cells. Columns 3-6 are user-defined parameters supplied to CIRIsimulator. Minimum circRNA size used in simulation: 50 bp. Pos: positive

50

TABLE 1B

Simulation dataset parameters with 18 datasets.

| Simulation set | Simulation dataset name | Average # of circRNA supporting reads | Range of # circRNA supporting reads | Average # of linear RNA supporting reads | Read length (bp) | # of reads generated | Window lengths tested (bp) | Overlapping base thresholds tested (bp) | # of candidates passing top 2% expression cut-off | # of candidates below bottom 1% expression cut-off |
|---|---|---|---|---|---|---|---|---|---|---|
| 1 | pos_2_80_150 | 2 | 2 to 11 | 80 | 150 | 30,926,238 | 300, 600 | 60, 40, 20, 10 | 1,196 | 13,176 |
| 2 | pos_2_80_100 | 2 | 2 to 10 | 80 | 100 | 46,264,524 | 300, 600 | 60, 40, 20, 10 | 1,616 | 12,829 |
| 3 | pos_2_80_50 | 2 | 2 to 13 | 80 | 50 | 92,271,226 | 300, 600 | 60, 40, 20, 10 | 620 | 12,670 |
| 4 | pos_5_40_150 | 5 | 2 to 17 | 40 | 150 | 22,725,820 | 300, 600 | 60, 40, 20, 10 | 712 | 5,261 |
| 5 | pos_5_40_100 | 5 | 2 to 18 | 40 | 100 | 33,962,378 | 300, 600 | 60, 40, 20, 10 | 944 | 3,887 |
| 6 | pos_5_40_50 | 5 | 2 to 17 | 40 | 50 | 67,667,118 | 300, 600 | 60, 40, 20, 10 | 1,296 | 4,122 |

TABLE 1B-continued

Simulation dataset parameters with 18 datasets.

| Simulation set | Simulation dataset name | Average # of circRNA supporting reads | Range of # circRNA supporting reads | Average # of linear RNA supporting reads | Read length (bp) | # of reads generated | Window lengths tested (bp) | Overlapping base thresholds tested (bp) | # of candidates passing top 2% expression cut-off | # of candidates below bottom 1% expression cut-off |
|---|---|---|---|---|---|---|---|---|---|---|
| 7 | pos_10_20_150 | 10 | 3 to 28 | 20 | 150 | 24,867,386 | 300, 600 | 60, 40, 20, 10 | 1,238 | 1,391 |
| 8 | pos_10_20_100 | 10 | 2 to 27 | 20 | 100 | 37,173,692 | 300, 600 | 60, 40, 20, 10 | 1,628 | 1,802 |
| 9 | pos_10_20_50 | 10 | 2 to 26 | 20 | 50 | 74,092,068 | 300, 600 | 60, 40, 20, 10 | 1,069 | 1,641 |
| 10 | pos_20_10_150 | 20 | 5 to 40 | 10 | 150 | 39,314,956 | 300, 600 | 60, 40, 20, 10 | 1,456 | 1,304 |
| 11 | pos_20_10_100 | 20 | 4 to 42 | 10 | 100 | 58,844,010 | 300, 600 | 60, 40, 20, 10 | 1,020 | 1,039 |
| 12 | pos_20_10_50 | 20 | 4 to 41 | 10 | 50 | 117,432,918 | 300, 600 | 60, 40, 20, 10 | 1,405 | 1,047 |
| 13 | pos_40_5_150 | 40 | 8 to 65 | 5 | 150 | 73,285,586 | 300, 600 | 60, 40, 20, 10 | 1,413 | 1,303 |
| 14 | pos_40_5_100 | 40 | 11 to 68 | 5 | 100 | 109,808,870 | 300, 600 | 60, 40, 20, 10 | 1,775 | 1,246 |
| 15 | pos_40_5_50 | 40 | 10 to 74 | 5 | 50 | 219,344,762 | 300, 600 | 60, 40, 20, 10 | 1,480 | 895 |
| 16 | pos_80_2_150 | 80 | 15 to 119 | 2 | 150 | 143,598,648 | 300, 600 | 60, 40, 20, 10 | 1,507 | 1,115 |
| 17 | pos_80_2_100 | 80 | 22 to 120 | 2 | 100 | 215,278,690 | 300, 600 | 60, 40, 20, 10 | 1,746 | 897 |
| 18 | pos_80_2_50 | 80 | 27 to 115 | 2 | 50 | 430,284,334 | 300, 600 | 60, 40, 20, 10 | 1,493 | 960 |

* All simulation datasets are based on data generated from human cerebellum and diencephalon, SH-SY5Y cells, Hs68 cells, HeLa cells, and HEK293 cells. Columns 3, 5 and 6 are user-defined parameters supplied to CIRI-simulator. Minimum circRNA size used in simulation: 50 bp, insert size used in simulation: 300 bp.

TABLE 2

Summary of experimental, non-simulated datasets used in this study.

| Data source | Dataset | Cell line/tissue type | RNase Rtreated? | Number of reads | Number of mapped reads | Median insert size |
|---|---|---|---|---|---|---|
| SRA | SRR1636985 | HeLa | Yes | 26,619,490 | 24,370,337 | 200 |
|  | SRR1637089 | HeLa | No | 89,866,900 | 63,842,205 | 140 |
|  | SRR1636986 | HeLa | Yes | 47,011,426 | 42,027,801 | 200 |
|  | SRR1637090 | HeLa | No | 71,370,620 | 53,957,685 | 130 |
|  | SRR444974 | Hs68 | Yes | 316,611,710 | 271,345,091 | 160 |
|  | SRR444655 | Hs68 | No | 314,106,316 | 109,706,923 | 150 |
| In-house generated | MG_1 | MTG | Yes | 107,609,934 | 96,300,242 | 150 |
|  | MG_5 | MTG | No | 96,215,516 | 86,315,844 | 150 |
|  | MG_2 | MTG | Yes | 96,840,790 | 86,560,619 | 150 |
|  | MG_6 | MTG | No | 101,609,754 | 90,750,108 | 150 |
|  | MG_3 | MTG | Yes | 111,576,344 | 100,264,691 | 150 |
|  | MG_7 | MTG | No | 111,314,114 | 98,894,498 | 150 |

SRA: Sequence Read Archive

TABLE 3

Summary of ACValidator results on experimental datasets.

| Dataset | # overlap with pair | # not depleted | # validated HS | MS | LS | VLS | % HS | MS | LS | VLS |
|---|---|---|---|---|---|---|---|---|---|---|
| SRR1636985 | 1,356 | 1,243 | 73.53 | 78.52 | 79.00 | 79.57 | 73.45 | 78.84 | 79.57 | 80.13 |
| SRR1637089 | 1,356 | 1,243 | 46.34 | 49.56 | 50.20 | 51.25 | 44.97 | 49.88 | 50.52 | 51.65 |
| SRR1636986 | 780 | 594 | 79.46 | 84.68 | 85.35 | 86.03 | 80.81 | 86.36 | 87.21 | 87.71 |
| SRR1637090 | 780 | 594 | 48.48 | 54.21 | 55.39 | 55.56 | 48.32 | 55.22 | 56.23 | 56.57 |
| SRR444974 | 953 | 864 | 91.55 | 93.63 | 93.98 | 94.33 | 89.93 | 92.01 | 92.48 | 92.82 |
| SRR444655 | 953 | 864 | 51.74 | 54.98 | 55.21 | 56.60 | 53.36 | 56.94 | 57.18 | 58.91 |
| MG_1 | 1,806 | 1,691 | 72.80 | 77.05 | 77.94 | 78.83 | 71.67 | 77.35 | 78.00 | 78.71 |
| MG_5 | 1,806 | 1,691 | 41.40 | 48.14 | 48.97 | 49.56 | 41.34 | 48.79 | 49.67 | 50.38 |
| MG_2 | 1,430 | 1,331 | 71.90 | 76.86 | 77.46 | 78.14 | 69.72 | 76.11 | 76.63 | 77.31 |
| MG_6 | 1,430 | 1,331 | 40.50 | 47.71 | 48.31 | 49.29 | 40.35 | 47.03 | 47.63 | 48.76 |
| MG_3 | 1,292 | 1,148 | 71.95 | 76.74 | 77.53 | 78.48 | 70.38 | 75.87 | 76.83 | 77.70 |
| MG_7 | 1,292 | 1,148 | 44.08 | 51.48 | 52.26 | 53.40 | 44.51 | 51.39 | 52.18 | 53.57 |

The "# overlap with pair " column lists the number of circRNAs in common between the RNase R-treated and non-treated samples.
The "# not depleted" column lists the number of circRNAs from the overlap whose normalized read counts, i.e., spliced reads per billion mapping (SRPBM) value does not reduce following RNase R-treatment (i.e., SRPBM after treatment > SRPBM before treatment).
HS: high stringency;
MS: medium stringency;
LS: low stringency;
VLS: very low stringency.

TABLE 4

ACValidator and other tools results on top 100 candidates from experimental datasets.

| Sample | CIRI_ count | CIRCexplorer_ count | findCirc_ count | Mapsplice_ count | KNIFE_ count | DCC_ count | HS_ count | MS_ count | LS_ count | VLS_ count |
|---|---|---|---|---|---|---|---|---|---|---|
| SRR1636985 | 99 | 93 | 89 | 97 | 92 | 92 | 94 | 97 | 97 | 97 |
| SRR1637089 | 99 | 92 | 87 | 97 | 92 | 92 | 74 | 78 | 79 | 79 |
| SRR1636986 | 99 | 95 | 84 | 96 | 95 | 92 | 91 | 91 | 93 | 94 |
| SRR1637090 | 95 | 88 | 57 | 85 | 95 | 83 | 71 | 77 | 78 | 78 |
| SRR444974 | 99 | 97 | 91 | 97 | 95 | 95 | 97 | 98 | 98 | 98 |
| SRR444655 | 99 | 97 | 76 | 38 | 95 | 90 | 84 | 84 | 84 | 84 |
| MG_1 | 40 | 96 | 85 | 99 | 91 | 88 | 91 | 94 | 94 | 94 |
| MG_5 | 55 | 93 | 72 | 98 | 91 | 80 | 77 | 83 | 83 | 83 |
| MG_2 | 35 | 96 | 90 | 100 | 90 | 90 | 89 | 93 | 93 | 93 |
| MG_6 | 50 | 92 | 68 | 98 | 90 | 82 | 75 | 81 | 81 | 81 |
| MG_3 | 44 | 96 | 83 | 99 | 88 | 88 | 90 | 93 | 94 | 94 |
| MG_7 | 40 | 94 | 79 | 99 | 88 | 85 | 84 | 88 | 91 | 91 |

The top 100 most highly expressed candidates were selected from the list of circRNAs called by at least three of six tools, in both treated and non-treated samples, and having SRPBM after RNase R treatment > SRPBM before treatment. Each < tool_name > _count column lists the number of circRNAs among the top 100 detected by the tool. Similarly, HS, MS, LS and VLS count columns list the number of circRNAs among the top 100 that were validated by ACValidator using those stringency thresholds.

REFERENCES

1. Beach, T. G., et al. Arizona study of aging and neurodegenerative disorders and brain and body donation program. *Neuropathology* 2015; 35(4):354-89.
2. Capel, B., et al. Circular transcripts of the testis-determining gene Sry in adult mouse testis. *Cell* 1993; 73(5): 1019-30.
3. Chen, I., Chen, C. Y. and Chuang, T. J. Biogenesis, identification, and function of exonic circular RNAs. *Wiley interdisciplinary reviews. RNA* 2015; 6(5): 563-79.
4. Cheng, J., Metge, F. and Dieterich, C. Specific identification and quantification of circular RNAs from sequencing data. *Bioinformatics* 2016; 32(7): 1094-96.
5. Du, W. W., et al. Foxo3 circular RNA promotes cardiac senescence by modulating multiple factors associated with stress and senescence responses. *European heart journal* 2016; 38(18): 1402-12.
6. Gao, Y., Wang, J. and Zhao, F. CIRI: an efficient and unbiased algorithm for de novo circular RNA identification. *Genome biology* 2015; 16: 4-014-0571-0573.
7. Glazar, P., Papavasileiou, P. and Rajewsky, N. circBase: a database for circular RNAs. *RNA (New York, N.Y.)* 2014; 20(11):1666-70.
8. Haas, B. J., et al. De novo transcript sequence reconstruction from RNA-seq using the Trinity platform for reference generation and analysis. *Nature protocols* 2013; 8(8):1494.
9. Hansen, T. B., et al. Natural RNA circles function as efficient microRNA sponges. *Nature* 2013; 495(7441): 384-88.
10. Hansen, T. B., et al. Comparison of circular RNA prediction tools. *Nucleic Acids Res* 2016; 44(6): e58.
11. Hansen, T. B., et al. miRNA-dependent gene silencing involving Ago2-mediated cleavage of a circular antisense RNA. *The EMBO journal* 2011; 30(21): 4414-22.
12. Jeck, W. R., et al. Circular RNAs are abundant, conserved, and associated with ALU repeats. *RNA (New York, N.Y.)* 2013; 19(2):141-57.
13. Koressaar T, Remm M (2007) Enhancements and modifications of primer design program Primer3 *Bioinformatics* 23(10):1289-91.
14. Langmead, B. and Salzberg, S. L. Fast gapped-read alignment with Bowtie 2. *Nature methods* 2012; 9(4):357-59.
15. Leinonen, R., et al. The Sequence Read Archive. *Nucleic Acids Research* 2011; 39(Database issue): D19-D21.
16. Li, H. Aligning sequence reads, clone sequences and assembly contigs with BWA-MEM. *arXiv preprint arXiv:* 1303.3997 2013.
17. Li, H., et al. The Sequence Alignment/Map format and SAMtools. *Bioinformatics* 2009; 25(16): 2078-79.
18. Li, Z., et al. Exon-intron circular RNAs regulate transcription in the nucleus. *Nature structural & molecular biology* 2015; 22(3): 256-64.
19. Memczak, S., et al. Circular RNAs are a large class of animal RNAs with regulatory potency. *Nature* 2013; 495(7441): 333-38.
20. Memczak, S., et al. Identification and Characterization of Circular RNAs As a New Class of Putative Biomarkers in Human Blood. *PLoS ONE* 2015; 10(10): e0141214.
21. Salzman, J., et al. Cell-type specific features of circular RNA expression. *PLoS genetics* 2013; 9(9): e1003777.
22. Salzman, J., et al. Circular RNAs are the predominant transcript isoform from hundreds of human genes in diverse cell types. *PloS one* 2012; 7(2): e30733.
23. Szabo, L., et al. Statistically based splicing detection reveals neural enrichment and tissue-specific induction of circular RNA during human fetal development. *Genome biology* 2015; 16:126-015-0690-0695.
24. Szabo, L. and Salzman, J. Detecting circular RNAs: bioinformatic and experimental challenges. *Nature reviews. Genetics* 2016; 17(11):679-92.
25. Untergasser A, Cutcutache I, Koressaar T, Ye J, Faircloth B C, Remm M, Rozen S G (2012) Primer3—new capabilities and interfaces. *Nucleic Acids Research* 40(15): e115.
26. Wang, K., et al. MapSplice: accurate mapping of RNA-seq reads for splice junction discovery. *Nucleic acids research* 2010; 38(18): e178.
27. Westholm, J. O., et al. Genome-wide analysis of drosophila circular RNAs reveals their structural and sequence properties and age-dependent neural accumulation. *Cell reports* 2014;9(5): 1966-80.
28. Zeng, X., et al. A comprehensive overview and evaluation of circular RNA detection tools. *PLoS computational biology* 2017; 13(6): e1005420.
29. Zhang, X. O., et al. Complementary sequence-mediated exon circularization. *Cell* 2014; 159(1):134-47.

We claim:

1. A bioinformatics method of selecting a circRNA for further analysis comprising:
receiving with a processor:
a sequence file of a dataset comprising RNA sequencing reads,
a reference genome, and
a circRNA junction;
extracting start-reads and end-reads from the sequence file with the processor;
generating a plurality of contigs by assembling the start-reads and end-reads with the processor;
extracting a start-sequence and an end-sequence from the reference genome with the processor;
concatenating the start-sequence and the end-sequence into at least one pseudo-reference;
aligning the plurality of contigs with the at least one pseudo-reference; and
selecting the circRNA for performing functional studies for the circRNA if the plurality of contigs overlaps with the at least one pseudo-reference above a threshold stringency and the threshold stringency requires a minimum of a 10-bp overlap between the plurality of contigs and the at least one pseudo-reference on either side of the circRNA junction;
wherein the functional study comprises (i) use of the circRNA as a probe to identify a biomolecule that binds to the circRNA; (ii) querying of circRNA sequences against known gene sequences to identify genes or transcripts that are regulated by specific circRNAs; (iii) knock-down or knock-out of the circRNA studies; or (iv) determining the in vivo functional consequence of loss-of-function circRNA phenotype.

2. The method of claim 1, further comprising performing RNA-Seq or whole transcriptome shotgun sequencing of RNA from a biological sample to obtain the RNA sequencing reads.

3. The method of claim 2, wherein the RNA is non-polyA selected.

4. The method of claim 2, wherein the RNA is treated with an exoribonuclease and the exoribonuclease is RNase R.

5. The method of claim 2, wherein the biological sample is blood, plasma, serum, saliva, urine, sputum, ascites, semen, bronchial lavage fluid, synovial fluid, cerebrospinal fluid, cells, or tissue.

6. The method of claim 1, wherein the circRNA is exonic or intergenic.

7. The method of claim 1, wherein the circRNA junction has been identified by a circRNA detection algorithm and/or the circRNA junction is annotated.

8. The method of claim 1, wherein the circRNA is at least 50 bp.

9. The method of claim 1, wherein the sequence file comprises at least five million reads.

10. The method of claim 1, wherein the length of the at least one pseudo-reference is about 4 times the length of an insert size from a sequencing library produced with RNA-Seq or whole transcriptome shotgun sequencing in the sequence file.

11. The method of claim 1, wherein at least two end-reads and start-reads are extracted.

12. The method of claim 1, wherein the dataset has a read length of at least 50 bp.

13. The method of claim 1, further comprising determining if the overlap between the plurality of contigs and the at least one pseudo-reference is above a threshold stringency and the threshold stringency requires a minimum of a 20-bp overlap between the plurality of contigs and the at least one pseudo-reference on either side of the circRNA junction.

14. The method of claim 1, wherein the processor comprises a Linux-based high-performance computing cluster and the processor is capable of distributing data to an individual node within the cluster with an aggregate throughput of about 9 GB/sec.

15. The method of claim 1, further comprising experimentally validating the circRNA wherein polymerase chain reaction (PCR) is used to detect the presence of the circRNA, quantify the abundance of the circRNA, or both.

16. The method of claim 1, wherein a biomolecule that binds to the circRNA is identified, the biomolecule is a microRNA (miRNA), and a miRNA binding site on the circRNA is identified based on complementarity of a sequence of the circRNA with a miRNA seed region.

17. The method of claim 1, wherein the function of the circRNA is determined from a loss-of-function phenotype or the functional studies of the circRNA comprise overexpression and/or knock-down of the circRNA.

18. The method of claim 1, wherein extracting the start-sequence and the end-sequence from the reference genome with the processor, the start-sequence and the end-sequence being non-colinear with each other and extracted from different sides of the circRNA junction.

* * * * *